United States Patent
Akala

(10) Patent No.: US 11,986,557 B2
(45) Date of Patent: May 21, 2024

(54) STEALTH NANOPARTICLES

(71) Applicant: HOWARD UNIVERSITY, Washington, DC (US)

(72) Inventor: Emmanuel Oyekanmi Akala, Mitchellville, MD (US)

(73) Assignee: HOWARD UNIVERSITY, Washington, DC (US)

( * ) Notice: Subject to any disclaimer, the term of this patent is extended or adjusted under 35 U.S.C. 154(b) by 0 days.

(21) Appl. No.: 16/698,297

(22) Filed: Nov. 27, 2019

(65) Prior Publication Data

US 2020/0163884 A1 May 28, 2020

Related U.S. Application Data

(60) Provisional application No. 62/772,489, filed on Nov. 28, 2018.

(51) Int. Cl.
| | | |
|---|---|---|
| *A61K 9/14* | (2006.01) | |
| *A61K 31/337* | (2006.01) | |
| *A61K 31/395* | (2006.01) | |
| *A61K 47/10* | (2017.01) | |
| *A61K 47/18* | (2017.01) | |
| *A61K 47/34* | (2017.01) | |
| *A61P 35/00* | (2006.01) | |
| *B82Y 5/00* | (2011.01) | |
| *B82Y 30/00* | (2011.01) | |
| *B82Y 40/00* | (2011.01) | |

(52) U.S. Cl.
CPC ............ *A61K 9/146* (2013.01); *A61K 31/337* (2013.01); *A61K 31/395* (2013.01); *A61K 47/10* (2013.01); *A61K 47/18* (2013.01); *A61K 47/34* (2013.01); *A61P 35/00* (2018.01); *B82Y 5/00* (2013.01); *B82Y 30/00* (2013.01); *B82Y 40/00* (2013.01)

(58) Field of Classification Search
CPC ........ A61K 47/10; A61K 47/18; A61K 47/34; A61K 9/146; A61K 31/337; A61K 31/395; A61P 35/00; B82Y 40/00; B82Y 5/00; B82Y 30/00
See application file for complete search history.

(56) References Cited

U.S. PATENT DOCUMENTS

| 9,675,556 B2 * | 6/2017 | Akala | ............... A61K 31/7034 |
| 2012/0129797 A1 * | 5/2012 | Akala | .................... C08G 63/06 977/773 |
| 2013/0336889 A1 * | 12/2013 | Shieh | ...................... A61P 35/00 424/1.89 |
| 2020/0163884 A1 * | 5/2020 | Akala | .................. A61K 9/5146 |

OTHER PUBLICATIONS

Ogunwuyi et al., "D-Optimal mixture experimental design for stealth biodegradable crosslinked docetaxel-loaded poly-epsilon-caprolactone nanoparticles manufactured by dispersion polymerization", 2015, Pharmazie, vol. 70, pp. 165-176. (Year: 2015).*

Puri et al., "pH-Sensitive Polymeric Nanoparticles Fabricated by Dispersion Polymerization for the Delivery of Bioactive Agents", Mar. 1, 2017, Pharmaceutical Nanotechnology, vol. 5, No. 1, pp. 44-66. (Year: 2017).*

* cited by examiner

*Primary Examiner* — Michael B. Pallay
(74) *Attorney, Agent, or Firm* — Sughrue Mion, PLLC

(57) ABSTRACT

Provided is a method for preparing a drug loaded nanoparticle comprising: dissolving a macromonomer, a stabilizer and a crosslinker in a solvent to create a mixture; adding an initiator system to the mixture; dissolving a drug or combination of drugs in an organic phase containing the mixture; and recovering the drug loaded nanoparticle, a composition comprising the drug loaded nanoparticle prepared by the above method, and a method for treating cancer comprising administering the above composition to a subject in need thereof.

16 Claims, 19 Drawing Sheets

STEALTH NANOPARTICLES

CROSS-REFERENCE TO RELATED APPLICATIONS

This application claims priority from U.S. Application No. 62/772,489, filed Nov. 28, 2018, the disclosure of which is incorporated herein in its entirety by reference.

BACKGROUND OF THE INVENTION

Successful thorough treatment of cancer has been a challenge over the years. Past chemotherapy treatments involved the administration of single chemotherapeutic agents, which were usually poorly soluble and highly toxic. Studies have shown that administration of cytotoxic agents in combination is more effective than they are administered individually. Combination chemotherapy is a treatment method that utilizes the synergistic and additive effects of two or more chemotherapeutic agents in inducing apoptosis (programmed cell death).

Anticancer drug loaded nanoparticles are advantageous in ensuring the targeting of cancer cells to enhance systemic delivery. Stealth drug loaded nanoparticles also enhance the nanoparticle circulation time allowing them to reach the tumor site through the enhanced permeation and retention effect (EPR). Nanotechnology as a drug delivery system also helps to overcome the problems associated with drug poor solubility, side effects and drug resistance.

The ingenious idea of utilizing the benefits of both worlds to have combination drug loaded nanoparticles seek to overcome the limitations of free drug combination chemotherapy and that of single drug-loaded nanoparticles.

According to the American Cancer Society, there is an expected estimation of 268,600 and 2,670 new cases of invasive breast cancer diagnosis in women and men in the United States (US) respectively for the year 2019. Further, there is a 1 in 8 chance that a woman in the US will be diagnosed with breast cancer, which also currently has a predicted mortality rate of 15.3% (1). Breast cancer occurs when the genes responsible for cell growth undergo mutation, resulting in rapid uncontrollable cell growth in the breast cells, which in turn develop into malignant tumors (2). Risk factors such as gene mutation, gender, estrogen, age, unhealthy lifestyle and family history, increase the chance of breast cancer development (3). There are different types of breast cancer that women, and in some cases men, suffer from. Some of which include estrogen-positive, HER2-positive, progesterone positive, triple-negative, and triple-positive (4, 5). These cancers are named based on the type of receptors expressed on their surfaces (6, 7).

Many drugs have been developed for cancer treatment, but unfortunately most of these drugs come with major side effects. The inability to target the diseased cells in the delivery method of these drugs presents other risk factors. Such risk factors may include cytotoxicity in healthy cells resulting from non-selectivity in cell exposure to drug. Cancer patients usually suffer more from the side effects of treatment, in most instances, than from the disease itself. It is highly imperative that better treatment methods are developed to help minimize or eliminate all the side effects and other impediments associated with cancer treatment.

The common forms of cancer treatments currently readily available include surgery, chemotherapy, radiation therapy, immunotherapy, hormone therapy, stem cell transplants and therapeutic vaccines. These are all effective cancer treatment methods. However, depending on the type or stage of the cancer, cancer patient may have to undergo a combination of two or more of these treatments for long or short terms to increase the occurrence of cell death. For example, early noninvasive breast cancer treatment where the tumor is in situ, adjuvant chemotherapy may be administered post-surgery to increase survival rate (8).

Chemotherapy is the treatment of cancer with anticancer drugs and is used to slow the growth of cancer cells, prevent the spread of cancerous cells to other parts of the body, shrink tumors, and prevent reoccurrence. Although this treatment method is effective, it brings on many side effects, which are detrimental to the quality of life of the patient (9).

Basically, drug combination chemotherapy is the use of more than one single drug during chemotherapy. The rationale for drug combination chemotherapy is to use drugs that work by different mechanisms, in order to block multiple pathways of cancer growth and survival. This system thereby reduces the likelihood of drug resistance and tumor reoccurrence (10). When drugs with different modes of action (MOA) are combined, each drug can be used at its optimal dose, without intolerable side effects (11).

Combination chemotherapy is currently being greatly explored due to the great advantages it presents to treatment that are lacking in single drug administration. Benefits such as lower drug doses that in turn minimize toxicity and side effects; emergence of synergistic or additive effects from interactions between the combined drugs and their different modes of action. When drugs of different MOA are combined, different signaling pathways can be targeted at the same time, facilitating their ability to overcome multidrug resistance (12). Drug combinations also allow decrease in number of administrations, which subsequently increases patient compliance (13).

Conventional or traditional combination chemotherapy which involves the co-administration by infusion of two or more cytotoxic agents of different mechanism of action has been proven to be effective but is associated with limitations such as toxicity and drug resistance issues (14). These complications are mostly outcomes of non-specificity in targeting diseased cells, increased susceptibility of drugs to protein binding (efflux transporters), reduced blood circulation half-lives, as well as poor drug solubility and physical stability (15) (16, 17).

The use of nanotechnology to achieve the benefits of combination chemotherapy seeks to overcome all the outlined problems associated with traditional/conventional combination chemotherapy.

A lot of research has been done and measures taken to ensure that nanoparticles are safe, biodegradable and efficient when administered to the body. Multiple studies, have indicated that stealth crosslinked polymeric nanoparticles, which are also biodegradable and biocompatible, can be used to achieve drug targeting, controlled release of therapeutic agents, tumor imaging, and solve the issue of drug resistance (18). These properties of stealth nanoparticles can be used to achieve the goals of improve drug solubility and physical stability, reducing the frequency in dosage of therapeutic agent, increasing patient compliance, and enhancing tumor accumulation throughout the treatment period by way of targeted delivery, reducing and hopefully eliminating most of the side effects of cancer treatment, ultimately reducing the time allocated to treatment and improving the quality of life of the patient.

The cellular microenvironment (CME) of breast cancer cells are generally acidic in nature (19); hence the use of pH sensitive crosslinkers in the fabrication of stealth acid-labile crosslinked polymeric nanoparticles will enhance effective drug-tumor targeting and drug release facilitated by EPR. The ability of the nanoparticle to effectively reach the diseased cell is a great achievement; however, it will be fruitless if the encapsulated or entrapped drug cannot be effectively released from the nanoparticle into the cell, after it has been endocytosed. Therefore, it is highly imperative that the nanoparticle is designed in a manner that facilitates effective release of the drug. Crosslinking agents facilitate controlled polymer degradation and drug release from nanoparticles. They also increase the mechanical strength of nanoparticles, which in turn causes reduced swelling, and diffusion of encapsulated drug from the polymer matrix (20).

Several approaches have been adapted in the development of pH sensitive nanosystems. These systems can be developed based on titratable groups or acid degradable linkages such as acetal groups which are stable under basic and neutral conditions but hydrolyze under acidic conditions (21-23). After studying the hydrolysis rate of di (2-methacryloyloxyethoxy)-[2,4-dimethoxyphenyl]methane, which is a pH sensitive acetal crosslinker, Puri et al determined that the crosslinker hydrolyzes much faster at pH 5.0 than at pH 7.4. This shows that the crosslinker is relatively stable at physiological pH but hydrolyzes in acidic environments (24).

SUMMARY OF THE INVENTION

Example embodiments of the inventive concept provide for a method for preparing a drug loaded nanoparticle comprising: dissolving a macromonomer, a stabilizer and a crosslinker in a solvent to create a mixture; adding an initiator system to the mixture; dissolving a drug in an organic phase containing the mixture; and recovering the drug loaded nanoparticle, a composition comprising the drug loaded nanoparticle prepared by the above method, and a method for treating cancer comprising administering the above composition to a subject in need thereof.

Due to the heterogeneity and complexity of cancer cells, focus on combination therapies capable of targeting multiple key pathways simultaneously are now on the rise. Polymeric nanoparticles have been known to facilitate targeted delivery of bioactive agents to the biophase. Nanotechnology as a platform for combination chemotherapy would greatly reduce toxicity and its associated side effects.

In order to solve the problem above, the present inventor investigated the effectiveness, importance and benefits of paclitaxel and 17-AAG loaded stealth polymeric nanoparticles, fabricated by dispersion polymerization, in breast cancer combination chemotherapy, and statistically analyzed the probable effectiveness of loading the two anticancer drug combination through this same platform for successful breast cancer treatment.

In particular, a pH-sensitive crosslinker and poly-ε-caprolactone macromonomer were successfully synthesized, characterized and used in the fabrication of blank and drug-loaded nanoparticles. The particle size, surface charge, surface morphology, drug loading, encapsulation efficiency, and drug release profiles of the nanoparticles were analyzed. Statistical experimental design (central composite face centered) and numerical and graphical optimizations of fabricated nanoparticles were carried out.

Particle size analysis revealed particle sizes in nanometer range, zeta potential analysis showed the nanoparticles have a negative surface charge. The scanning electron micrograph showed the particles were spherical. The drug loading analysis, encapsulation analysis and drug release profiles showed that both paclitaxel and 17-AAG were effectively loaded and successfully released from the nanoparticles.

The synthesized polymeric nanoparticles are a stable platform for the effective delivery of drug combinations to cancer cells. Statistical analyses of the nanoparticle formulations reveal the crosslinker and PEG amounts significantly contribute to the nanoparticle formulation outcomes.

DETAILED DESCRIPTION OF THE INVENTION

Figure 1:
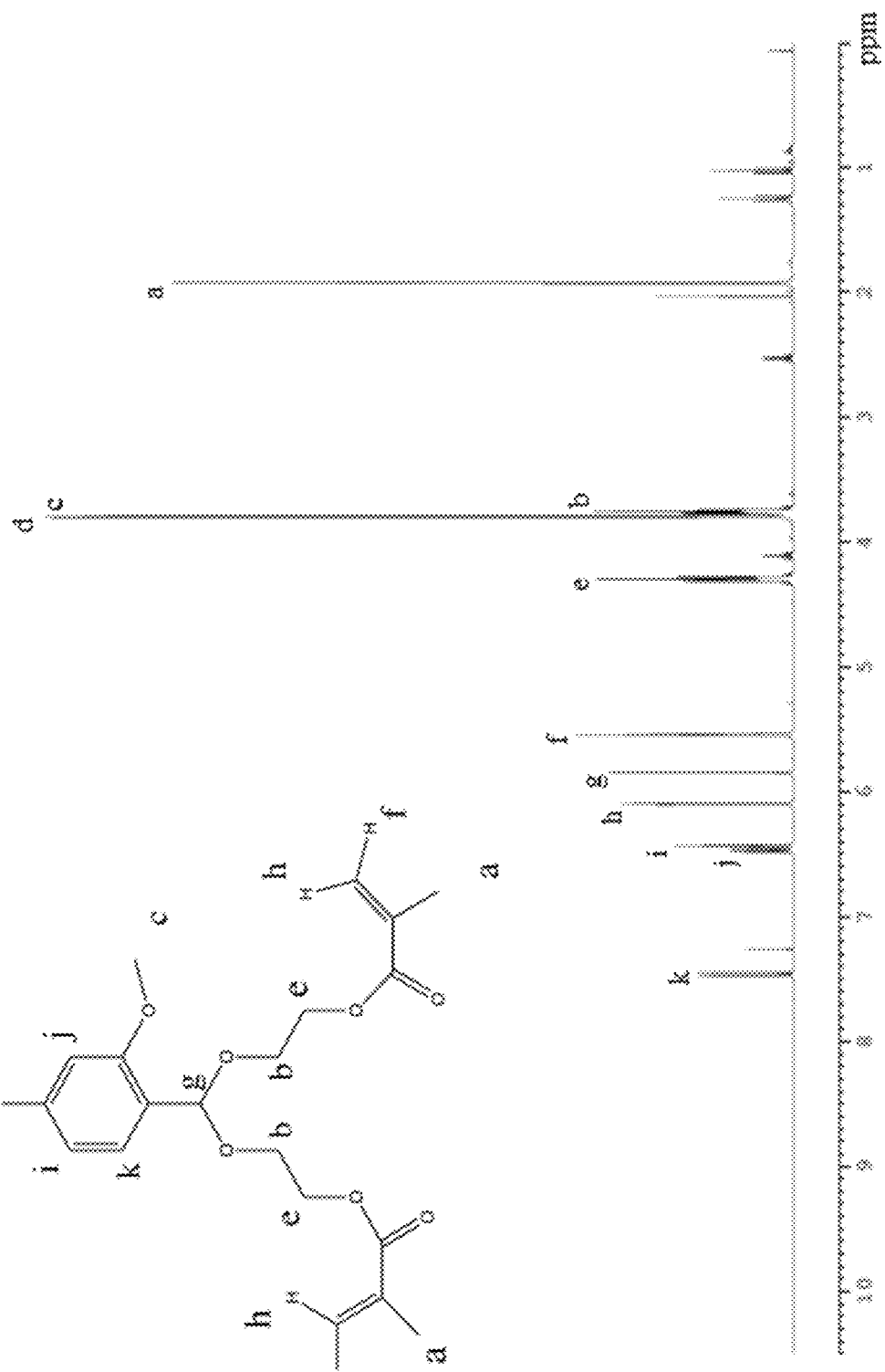
FIG. 1 shows the structure and 1H-NMR of Crosslinker (di (2-methacryloyloxyethoxy)-[2,4-dimethoxyphenyl]methane).

Example embodiments of the inventive concept will be described in detail in reference to the accompanying drawings. However, the inventive concept may be embodied in many different forms and is not construed as limited to the example embodiments set forth herein.

Example embodiments of the inventive concept provide for a method for preparing a drug loaded nanoparticle comprising: dissolving a macromonomer, a stabilizer and a crosslinker in a solvent to create a mixture; adding an initiator system to the mixture; dissolving a drug in an organic phase containing the mixture; and recovering the drug loaded nanoparticle, a composition comprising the drug loaded nanoparticle prepared by the above method, and a method for treating cancer comprising administering the above composition to a subject in need thereof.

According to an aspect of an example embodiment, the macromonomer is selected from the group consisting of polyglycolide (PGA) macromonomer, polylactide (PLA) macromonomer, polycaprolactone (PCL) macromonomer, poly(lactide-co-glycolide) (PLGA) macromonomer, poly (propylene fumarate) PFF, methacryloyl-teiminated PMMA macromonomer, methacrylate-teiminated/functionalized poly(dimethylsiloxane) macromonomer (PDMS-MA), methacryloylpolystyrene (MA-Pst) (i.e styrene macromonomers with methacryloyl end group), (vinylbenzyl)polystyrene (VB-Pst) (i.e styrene macromonomers with a vinylbenzyl end group), 2-oxyethylmethacrylate-terminated PLLA macromonomer (MC), vinylbenzyl-terminated polyisoprene (PI) macromonomers, poly(ethylene glycol)-co-poly(A-hydroxyacid) diacrylate macromers, oligocaprolactone vinyl ether macromonomer, PEG-PLA macromer, PEG-PLA-PEG macromer, poly(ethylene oxide) (PEO) block functionalized with styryl, methacryloyl, thiol, maleate, vinyl, p-vinylphenylalkyl reactive end groups, methacryloxypropyl- and vinyl-terminal polysiloxanes, α-methacryloylpoly(E-caprolactone) (PCL) macromonomer, poly(glycolide) macromonomers, HEMA terminated oligo(L-lactide) or oligo (D-lactide) macromonomers, oligoNIPAAm (oligo N-isopropylacrylamide) and polyNIPAAm (poly(N-isopropylacrylamide)) macromonomers, poly(n-butylacrylate) macromonomers, n-butyl acrylate, methyl acrylate (MA), methyl methacrylate (MMA), N,N'-dimethyl acrylamide (DMA); N-vinyl pyrrolidone (VP), hydroxyethyl methacrylate, n-butyl methacrylate, acrylamide, hydrophilic N-(2-hydroxypropylmethacrylamide) (HPMA), methyl-, ethyl- butyl-, octylcyanoacrylates (anionic polymerization) to form poly(alkylcyanoacrylates) (PACA) (biodegradable, pH sensitive), acrylic acid, 2-hydroxypropyl methacrylate (HPMA), N,N-dimethylaminoethyl methacrylate (DMAEMA), hydrophilic polymers or macromonomers, poly(vinyl pyrrolidone), (hydroxypropyl) cellulose (HPC), poly(acrylic acid), poly[N-(2-hydroxypropyl)methacrylamide] (PHMPA), dextrans, e.g. dextran-10, -40, -70, poloxamer-188, -184, -237, polyethylene glycol (PEG), polyethylene oxide (PEO) and PEO macromonomers with p-vinylbenzyl and methacrylate end groups, poloxamine, polysorbates, methacryloyl-terminated poly(ethylene oxide) macromonomer, poly(2-alkyl-2-oxazolin), poly(methacrylic acid), poly(acrylic acid) macromonomers, bifunctional vinyl urethane macromonomers, vinyl terminus polysiloxane macromonomer, poly(vinyl alcohol), polyacrylamide, and poly(glutaraldehyde).

According to an aspect of an example embodiment, the macromonomer is poly(epsilon-caprolactone).

According to an aspect of an example embodiment, the crosslinker is di (2-methacryloyloxyethoxy)-[2,4-dimethoxyphenyl]methane.

According to an aspect of an example embodiment, the stabilizer is polyethylene glycol.

According to an aspect of an example embodiment, the initiator system comprises benzoyl peroxide (BPO), azobis-isobutyronitrile (AIBN), potassium persulfate (KPS), 2,2'-azobis-2,4-dimethylvaleronitrile (ADVN), PDMS macroazoinitiator (PDMS-azo), ammonium persulfate, thermal 2,2'-azobis [N-(2-carboxyethyl)-2-2-methylpropionamidine](VA-057) (amphoteric pH sensitive initiator), redox initiators, and photoinitiators.

Examples of redox initiators include, but are not limited to, BPO activated by tertiary amines such as: N,N-dimethyl-4-toluidine (DMT), N,N-dimethylbenzyl methacrylate, N,N-dimethylbenzyl alcohol, N,N-dimethylaniline, 4-N,N-dialkyl aminophenalkanoic acids and their methyl esters, peroxides, persulfate, peroxomonosulfate, peroxidiphosphate, metal ion oxidant-reducing agent systems which include but are not limited to Mn(III) and Mn(VII), Ce(IV), V(V), Co(III), Cr(VI) and Fe(II and III).

Examples of photoinitiators include, but are not limited to 2,2-dimethoxy-2-phenylacetophenone, Quantacure ITX photosensitizer, Irgacure 907 (1-907) initiator systems, and N,N-dimethyl ethanol amine.

According to an aspect of an example embodiment, the initiator system comprises benzoyl peroxide and N-phenyldiethanolamine.

According to an aspect of an example embodiment, the solvent comprises dichloromethane, water, ethanol, hexane, ethyl acetate, acetone, dimethyl sulfoxide and tetrahydrofuran.

According to an aspect of an example embodiment, the drug comprises at least one selected from the group consisting of paclitaxel, doxorubicin, docetaxel, trastuzumab, pertuzumab, lapatinib and tanespimycin (17-AAG).

According to an aspect of an example embodiment, the drug comprises paclitaxel and tanespimycin (17-AAG).

According to an aspect of an example embodiment, the macromonomer is included in an amount of 0.224 mmol to 0.279 mmol.

According to an aspect of an example embodiment, the stabilizer is included in an amount of 0.898 mmol to 1.1225 mmol.

According to an aspect of an example embodiment, the initiator system is included in an amount of 0.594 mmol to 0.744 mmol.

According to an aspect of an example embodiment, the crosslinker is included in an amount of 0.373 mmol to 0.466 mmol.

Example embodiments of the inventive concept also provide for a composition comprising the drug loaded nanoparticle prepared by the above methods.

According to an aspect of an example embodiment, the drug included in the drug loaded nanoparticle comprises paclitaxel and tanespimycin (17-AAG).

Example embodiments of the inventive concept also provide for a method for treating cancer comprising administering the above composition to a subject in need thereof.

According to an aspect of an example embodiment, the cancer comprises stomach cancer, lung cancer, liver cancer, colorectal cancer, colon cancer, small intestinal cancer, pancreatic cancer, brain cancer, bone cancer, melanoma, breast cancer, sclerosing adenosis, uterine cancer, cervical cancer, head and neck cancer, esophageal cancer, thyroid cancer, parathyroid cancer, breast cancer, renal cancer, sarcoma, prostate cancer, urethral cancer, bladder cancer, blood cancer, leukemia, lymphoma, fibroadenoma, etc.

According to an aspect of an example embodiment, the cancer is breast cancer.

According to an aspect of an example embodiment, the cancer is HER2 positive breast cancer.

According to an aspect of an example embodiment, the drug included in the drug loaded nanoparticle comprises paclitaxel and tanespimycin (17-AAG).

According to an aspect of an example embodiment, an amount of the paclitaxel in the drug loaded nanoparticle is lower than its original concentration. For instance, the amount of the paclitaxel in the drug loaded nanoparticle is 5-95% of the original concentration of paclitaxel. The lower limit may be alternatively selected from 10%, 15%, 20%, 25%, 30%, 35%, 40%, 45%, 46%, 47%, 48%, 49%, 50%, 51%, 52%, 53%, 54%, 55%, 56%, 57%, 58%, 59%, 60%, 65%, 70%, 75%, 80%, 85% or 90%. The upper limit may be alternatively selected from 10%, 15%, 20%, 25%, 30%, 35%, 40%, 45%, 46%, 47%, 48%, 49%, 50%, 51%, 52%, 53%, 54%, 55%, 56%, 57%, 58%, 59%, 60%, 65%, 70%, 75%, 80%, 85% or 90%.

According to an aspect of an example embodiment, an amount of the paclitaxel in the drug loaded nanoparticle is half of its original concentration.

According to an aspect of an example embodiment, an amount of the tanespimycin (17-AAG) in the drug loaded nanoparticle is lower than its original concentration. For instance, the amount of the tanespimycin (17-AAG) in the drug loaded nanoparticle is 5-95% of the original concentration of tanespimycin (17-AAG). The lower limit may be alternatively selected from 10%, 15%, 20%, 25%, 30%, 35%, 40%, 45%, 46%, 47%, 48%, 49%, 50%, 51%, 52%, 53%, 54%, 55%, 56%, 57%, 58%, 59%, 60%, 65%, 70%, 75%, 80%, 85% or 90%. The upper limit may be alternatively selected from 10%, 15%, 20%, 25%, 30%, 35%, 40%, 45%, 46%, 47%, 48%, 49%, 50%, 51%, 52%, 53%, 54%, 55%, 56%, 57%, 58%, 59%, 60%, 65%, 70%, 75%, 80%, 85% or 90%.

According to an aspect of an example embodiment, an amount of the tanespimycin (17-AAG) in the drug loaded nanoparticle is half of its original concentration.

Example embodiments of the inventive concept also provide improved biodegradable stealth polymeric nanoparticles fabricated using the macromonomer approach by free radical dispersion polymerization described in U.S. Pat. No. 8,921,429, which is hereby incorporated by reference.

In particular, the nanoparticle described in the above patent has been improved upon to be multifunctional (with a targeting moiety to direct nanoparticles to where cancer is in the body using the receptor expressed uniquely on the cancer cells) and to incorporate combination drugs to overcome drug resistance.

According to an aspect of an example embodiment, there is provided trimodal combination multifunctional therapeutics nanoparticles which will prove more effective with less toxicity than current therapies for HER2 positive breast cancers. These trimodal multifunctional polymeric nanoparticles are of six types: within the core are at least two (low molecular weight) bioactive and each formulation will also be "decorated" on the surface with monoclonal antibodies already approved by the FDA as a targeting moiety to specifically target HER2 receptors and also to serve as a molecular targeted therapy. Such nanoparticles will bring to bear the combined power of chemotherapeutic agents and molecular targeted therapy using nanotechnology, to overcome HER2 resistance and breast cancer metastasis. According to an aspect of an example embodiment, there is provided: (i) a novel biocompatible, biodegradable, and hydrolysable polymeric carrier core for high drug loading efficiency and controlled release of encapsulated drugs in the core; and (ii) the tumor targeting monoclonal antibodies tethered to the surface of the polymeric nanoparticles for enhanced site-specific tumor delivery, internalization by receptor mediated endocytosis and molecular targeted therapy.

According to an aspect of an example embodiment, there is provided: (a) the combination drugs are poorly water soluble (incorporation into the poly(lactide) hydrophobic nanoparticle core will circumvent this problem); (b) coordinated delivery of the drugs encapsulated in the nanoparticle core and monoclonal antibodies targeted on the surface will have more favorable pharmacokinetics and arrive at the biophase in the tumors simultaneously, following receptor mediated endocytosis (varying biodistribution/pharmacokinetics of combination drugs through cocktail administration has been attributed to their ineffectiveness in the clinic); (c) in addition, clinical data support that concurrent therapy with for all the drugs is more effective than their sequential use; (d) further, the stealth property of the nanoparticles due to PEG on the surface will prevent opsonization and capture by the reticular endothelial system; (e) synergistic effects will be promoted by combination drugs; (f) the multifunctional polymeric nanoparticles will be capable of specific delivery of large amounts of bioactive agents per targeting biorecognition event compared to simple immunotargeted bioactive agents, that is antibody drug conjugates: ADCs; and (g) the embodiment is based on an in situ polymerization technique (dispersion polymerization) for the fabrication of core-shell nanoparticles. It will be carried out at an ambient temperature suitable for thermolabile compounds (proteins: monoclonal antibodies). proposed in this application. The fabrication of the nanoparticles is a one pot process (simultaneous encapsulation of drugs in the core and, by copolymerization, the addition of surface functionalities (tethering ligands (monoclonal antibodies)) or PEG to nanoparticle surface) in one batch process without further modifications compared to difficulty encountered (drug leaking) in nanoparticle fabrication from preformed polymers. The process is surfactant free; thereby obviating some of the side effects seen in Taxol® and Taxotere® due to surfactants. The above will bring to bear the combined power of chemotherapeutic agents and molecular targeted therapy via nanotechnology to overcome HER2 resistance with minimal toxicity. The providers and patients will be receptive to the product because of efficacy, elimination of resistance and cancer metastasis and lack of toxicity/side effects. The payers will reimburse the product at a reasonable price because the price is affordable. The drugs and monoclonal antibodies are already approved by the FDA. Getting the product to the market will be fast and at a small cost.

Other aspects of the invention include the embodiments as follows.

(A). Characterization of a single drug-loaded (paclitaxel and docetaxel) stealth nanoparticles made with biodegradable polymers (poly (L lactide) and separately with poly e caprolactone).

(B). Basis for clinical trial on the single drug-loaded (paclitaxel and docetaxel) nanoparticles.

(C). Animal work (biodistribution and efficacy studies) of combination drugs (paclitaxel+lapatinib; docetaxel+lapatinib; paclitaxel+17 AAG; and docetaxel+17 AAG), loaded in nanoparticles made from biodegradable polymers (poly (L lactide) and separately with poly e caprolactone).

(D). Characterization of the combination nanoparticles in (C) by collaboration with Nanotechnology Characterization Laboratory in Frederick, MD.

(E). Basis for clinical trial on combination nanoparticles in (C).

(F). Development of multifunctional polymeric nanoparticles which are of six types as follows: within the core are (paclitaxel+lapatinib; docetaxel+lapatinib; paclitaxel+17 AAG; and docetaxel+17 AAG), but each of combination formulation will also be "decorated" on the surface with trastuzumab on one hand and separately with pertuzumab on the other hand as a targeting moiety to specifically target HER 2 receptors and also to serve as molecular targeted therapy.

(F.1). Synthesis of stealth hydrolyzable crosslinked trastuzumab or pertuzumab surface-targeted P(LLA) nanoparticles loaded with combination drugs indicated in (F) above.

(F.2). Synthesis of stealth hydrolyzable crosslinked trastuzumab or pertuzumab surface-targeted-poly ε caprolactone nanoparticle loaded with combination drugs indicated in (F) above.

(F.3). Physicochemical characterization of the nanoparticles in (F.1) and (F.2) above.

(F.4). In vitro characterization of the nanoparticles in (F.1) and (F.2): HER2 affinity assay and HER2 binding with flow cytometry using SK BR 3 (HER2 overexpressing), MCF7 (low expression of HER2) and control: MDA MB 231 (no HER2 expression).

(F.5). Biodistribution and efficacy studies on combination drugs (paclitaxel+lapatinib; docetaxel+lapatinib; paclitaxel+ 17 AAG; and docetaxel+17 AAG)-loaded stealth trastuzumab or pertuzumab surface-targeted-P(LLA) or poly e caprolactone nanoparticles using female nude mice implanted subcutaneously with BT474 (HER2+), BT474/ Her2R (HER2+ resistant) or MDA MB 231 (HER2− Control) cell lines.

According to an aspect of an example embodiment, there is provided: (i) a novel biocompatible, biodegradable, and hydrolysable polymeric carrier core for high drug loading efficiency and controlled release of paclitaxel and docetaxel (cytotoxic drugs), lapatinib (molecular targeted therapy), and 17 AAG (HSP90 inhibitor); and (ii) the tumor targeting trastuzumab or pertuzumab tethered to the surface of the polymeric nanoparticles for enhanced site specific tumor delivery, internalization by receptor mediated endocytosis and molecular targeted therapy.

Other aspects of the invention include the embodiments as follows.

(A). Paclitaxel, docetaxel and 17 allylamino, 17 demethoxygeldanamycin (17 AAG) are poorly water soluble. Incorporation into the poly(lactide) or poly e caprolactone hydrophobic nanoparticle core will circumvent this problem.

(B). Coordinated delivery of paclitaxel, docetaxel, lapatinib and 17 AAG encapsulated in the nanoparticle core and trastuzumab or pertuzumab targeted on the surface will have more favorable pharmacokinetics and arrive at the biophase (site of action) in the tumors simultaneously, following receptor mediated endocytosis. Varying biodistribution/ pharmacokinetics of combination drugs through cocktail administration has been attributed to their ineffectiveness in the clinic.

(C). In addition, clinical data support that concurrent chemotherapy with trastuzumab or pertuzumab is more effective than sequential use of these agents. The embodiment will ensure concurrent therapy because all the bioactive agents are together in one nanoparticles.

(D). Further, the stealth property of the nanoparticles due to PEG trastuzumab or PEG pertuzumab on the surface will prevent opsonization and capture by the reticular endothelial system which is the drawback of the current nano-therapy.

(E). Synergistic effects will be promoted as exemplified by 17 AAG which has been reported to sensitize cancer cells to apoptosis induced by paclitaxel.

(F). The multifunctional and multivalent polymeric nanoparticles will be capable of specific delivery of large amounts of bioactive agents per targeting biorecognition event compared to simple immunotargeted bioactive agents, that is antibody drug conjugates: ADCs.

(G). The embodiment is based on an in situ polymerization technique (dispersion polymerization) for the fabrication of core-shell nanoparticles. It will be carried out at an ambient temperature suitable for thermolabile compounds (proteins: monoclonal antibodies) proposed in this application. The fabrication of the nanoparticles is a one pot process (simultaneous encapsulation of drugs in the core and, by copolymerization, the addition of surface functionalities (tethering ligands (monoclonal antibodies)) to nanoparticle surface) in one batch process without further modifications compared to difficulty encountered (drug leaking) in nanoparticle fabrication from preformed polymers. The process is surfactant free; thereby obviating some of the side effects seen in Taxol® and Taxotere® due to surfactants.

EXAMPLES

Materials and Methods
Materials 2,4-Dimethoxybenzaldehyde (DMBA) (98%), 2-Hydroxyethyl methacrylate (HEMA) (97%), Para-Tuolene-sulfonic acid monohydrate (PTSoh.H2O) ACS reagent (>98.5%), anhydrous dichloromethane (DCM) (>99.8%), trimethylamine (TEA) (>99%), molecular sieves 4 A° (1.6 mm diameter), chloroform D (99.8 atom % D), and ethyl acetate (ACS reagent plus) (99.8%), were all purchased from Sigma Aldrich (St. Louis, MO, USA) Hexane (95%) was purchased from The British Drug Houses (BDH Chemicals) through VWR (Atlanta, GA, USA). Activated basic aluminum oxide (58 A° pore size) was also obtained from Sigma Aldrich. Epsilon caprolactone monomer (99%), toluene (chromasolv, HPLC grade) (99.9%), calcium hydride, tin (II)-2 ethylheaxnoate (stannous octoate), tetrahydrofuran (HPLC grade), chloroform-D, phosphorous pentoxide and anhydrous dichloromethane were obtained from Sigma Aldrich. Stabilizer (poly(ethylene glycol)n (PEG) (n=1000) (Polysciences, Inc. (Warrington, PA, USA)), redox initiator system: benzoyl peroxide and N-phenyldiethanolamine (BPO/N-PDEA) (Sigma Aldrich), solvent acetone (HPLC grade), NaCl (Fisher scientific), NaOH pellets (Sigma Aldrich), and potassium phosphate monobasic (Sigma Aldrich). Both drugs, paclitaxel and 17AAG were obtained from LC Laboratories. Apart from HEMA, epsilon caprolactone monomer, and toluene that were distilled prior to use, all materials were used as received.

Methods

Synthesis of di (2-methacryloyloxyethoxy)-[2,4-dimethoxyphenyl]methane (pH Sensitive Crosslinker)

HEMA was dried over activated molecular sieves for 24 hours and distilled under negative pressure in an oil bath before use. More molecular sieves were activated in the oven at about 120° C. for 3 hours and placed in a round bottom flask containing a magnetic stirrer, together with a mixture of 3.9964 g of 2,4-Dimethoxybenzaldehyde (DMBA), 12 mL distilled HEMA, and 0.725 g Para-Tuolenesulfonic acid monohydrate (PTSoh.H2O). 30 mL anhydrous dichloromethane (DCM) was injected into the flask and stirred at room temperature under nitrogen gas for 30 minutes (24). The reaction was left to run for 24 hours, after which it was quenched by being placed in an ice bath and injecting 4.2 mL of triethylamine into the flask to neutralize the acidic catalyst used, as it continued to stir for 30 minutes more (at 0° C.). The final product was filtered with whatman filter paper (110 mm pore size and 6 μm particle retention), washed with dichloromethane, evaporated of solvent, and purified by column chromatography. Aluminum oxide was used as the stationary phase, while the mobile phase consisted of hexane/ethyl acetate (6:1) with 1% (v/v) trimethylamine.

Characterization of Acetal Crosslinker

Figure 2:
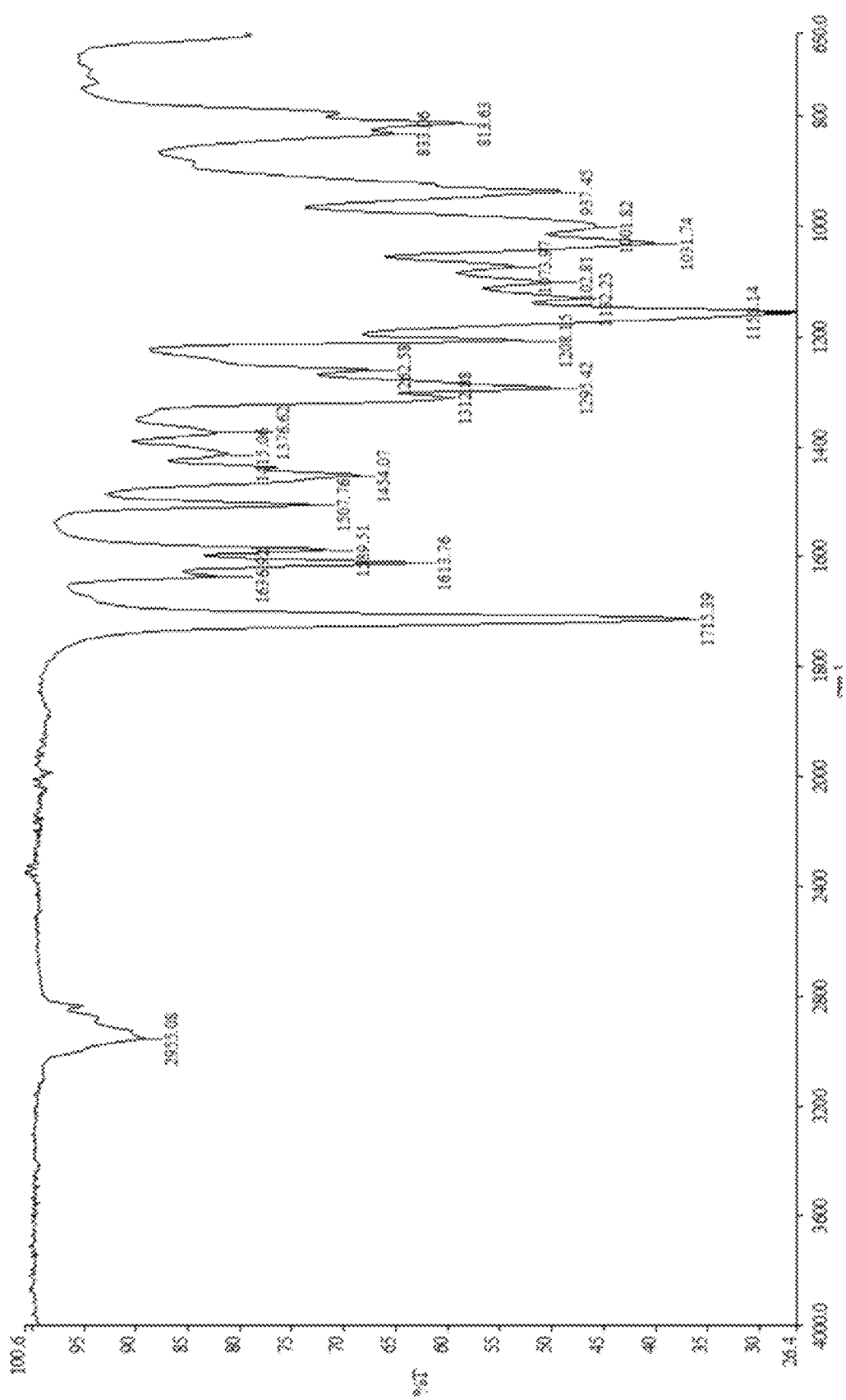
FIG. 2 shows a FT-IR spectra of Crosslinker (di (2-methacryloyloxyethoxy)-[2,4-dimethoxyphenyl]methane).

The crosslinker was dissolved in deuterated chloroform and analyzed by proton nuclear magnetic resonance (1H-NMR), using a Brooker ADVANCE 400 MHz NMR spectrophotometer. Fourier-transform infrared analysis of the synthesized crosslinker was also performed using a Perkin Elmer spectrum 100 FT-IR spectrophotometer. Liquid chromatography mass spectrometry (LC-MS) was used to determine the molecular weight of the crosslinker. See FIGS. 1 and 2.

Synthesis of Poly(ε-Caprolactone) Macromonomer

HEMA and epsilon caprolactone monomer were each dried over activated molecular sieves for 24 hours and distilled under negative pressure in an oil bath. Toluene was dried over calcium hydride for 1 hour, prior to distillation. Silicone oil bath was heated and equilibrated to 120° C., and 12.75 mL distilled e-caprolactone was polymerized in the presence of 2.8 mL distilled HEMA and 0.0375 mL of 0.4M stannous octanoate (stannous octanoate dissolved in distilled toluene) by ring opening polymerization. Prior to polymerization, the mixture was placed under vacuum for 10 minutes without stirring or heat, after which it was lowered into the oil bath set at 120° C. and stirred at 350 rpm. After 24 hrs, the reaction was removed from the oil bath and allowed to cool for a few minutes, after which 10 mL dichloromethane (DCM) was added. The product was added to 100 mL DCM and filtered through a Whatman filter paper (Cat. No.: 1001-110, particle retention: 1 μm) using a vacuum pump and a Buchner funnel (25). The filtrate was decanted into 1000 mL beaker after which cold hexane was added for the macromonomer to precipitate out. Precipitated product was filtered again, using the same type of filter paper.

Characterization of Poly(ε-Caprolactone) Macromonomer

Figure 3:
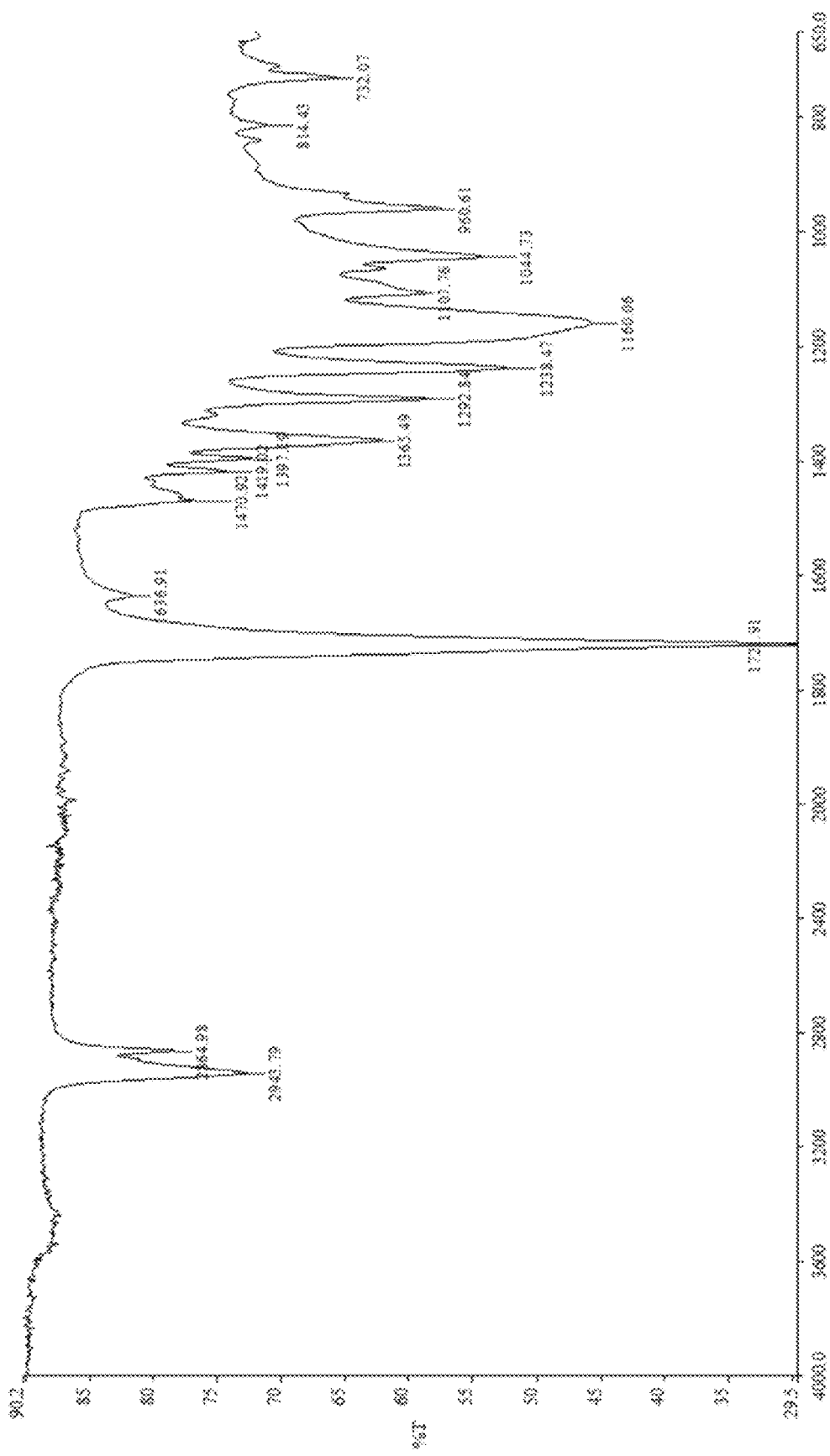
FIG. 3 shows a FT-IR spectra of poly(s-caprolactone) macromonomer (P(CL-HEMA))

The final product was dried in the vacuum oven at 25 mm Hg over phosphorous pentoxide (drying agent). Samples of the dried macromonomer were dissolved in chloroform-D and tetrahydrofuran for proton nuclear magnetic resonance (H1NMR) (400 Mhz) and gel permeation chromatography (GPC) (Waters 2690 with a Waters 2410 differential refractive index detector) respectively, to determine its purity and molecular weight. Polystyrene standards were used for calibration using GPC. The macromonomer was also characterized by Fourier transform infrared spectroscopy (FT-IR). See FIG. 3.

Fabrication of Blank and Drug-Loaded Nanoparticles

Using redox initiators, all nanoparticles were synthesized by the dispersion polymerization method, whereby all components are added in a single reaction yielding the formation of nanoparticles. In this type of nanoparticle, the drug and polymer form a matrix interconnected by a crosslinking agent.

In this method of nanoparticle synthesis, the initiator system introduces a free radical which starts a polymerization chain reaction, whereby the polymer chain propagates till it reaches saturation where the reaction is terminated. The reaction starts as a homogeneous solution and the polymerization chain reaction takes place in the continuous aqueous phase (25, 26). As the polymer chain continues to grow, it begins to precipitate out of solution forming nanoparticles from aggregated nuclei (27). The components of all formulations synthesized were within the constraints listed in Table 1. The redox initiator system was made of a 1:1 ratio of benzoyl peroxide/N-phenyldiethanolamine (BPO/NPDEA)

TABLE 1

Formulation Component Constraints

| Component | Lower Limit (mmol) | Upper Limit (mmol) |
| --- | --- | --- |
| Macromonomer | 0.224 | 0.279 |
| Stabilizer (PEG) | 0.898 | 1.1225 |
| Initiator System | 0.594 | 0.744 |
| Crosslinker | 0.373 | 0.466 |

Blank Nanoparticle Synthesis:

The required amounts of all materials (crosslinker, macromonomer, PEG, and redox initiator system (BPO/NPDEA)) were weighed into separate scintillation vials, dissolved in acetone and vortex mixed. The macromonomer was dissolved first, followed by the PEG and crosslinker in that order. D.I. water was pipetted into the mixture vial to create a colloidal solution, and vortexed. To clear up the turbidity, acetone was added to the vial in portions and vortex mixed. The mixture was then decanted into a 100 mL 3 neck round bottom flask (RBF) after sealing extreme ends with suba seal. Finally, the sealed RBF was stabilized on a stirring plate after which it was flashed with N2 gas for 10 mins before injecting the (BPO/N-PDEA) co-initiator system (dissolved in acetone), 10 mins apart. N2 gas was stopped after 6 hrs and the reaction was left to run for a total of 18 hours (24, 25, 28).

A 7.4 pH phosphate-buffered saline (PBS buffer) was prepared and the colloidal suspension formed was dialyzed using a 12-14 kDa molecular weight cut-off (MWCO) (Spectra/Por® CE) membrane, for two days. The PBS buffer which was the dialysis medium was changed 24 hrs after dialysis was initiated. The particles were lyophilized, weighed, characterized and stored at 4° C. when dialysis was complete (24, 25, 28).

Drug-loaded nanoparticles were synthesized with the same procedure for blank nanoparticles. However, 0.0171 mmols of each drug (paclitaxel and 17-AAG) was injected into the reaction after 4 hours. N2 gas was stopped after 6 hours and the reaction was allowed to run for a total of 18 hours.

Characterization of Drug Loaded Nanoparticles

Nanoparticles were characterized to determine their size, surface charge, surface morphology, drug loading capacity, drug encapsulation efficiency, and drug release profile.

Particle Size Analysis:

The average particle size was determined by dynamic light scattering (DLS) technique using a Brookhaven 90 plus particle size analyzer. Samples of the nanoparticle formulations were each diluted with deionized water, probe sonicated for 45 seconds, and filtered with a 5-micron syringe filter, into a cuvette before analyzing. Polydispersity index of the particles (a measure of particles size distribution) was also determined.

Zeta Potential 10 mg of freeze-dried nanoparticles were resuspended in deionized water, probe sonicated and filtered through a 5-micron syringe filter. 1 mL of the filtrate was diluted with 1 mL deionized water analyzed using a Brookhaven 90plus, Zetaplus zeta potential analyzer. For each sample, 5 measurements were taken, and their average determined.

Scanning Electron Microscopy (SEM)

After 2 minutes of gold coating, the morphology of the particles was determined by scanning electron microscope imaging using JOEL JSM 7600F (SEM). Images were taken from different magnifications and dilutions of observed particles, at 20 kV.

Drug Loading (DL)

To determine the percent loading of the drugs in the nanoparticles, 5 mg (ANp) of freeze-dried nanoparticles were dissolved in 5 mL acetonitrile, filtered with a 0.2-micron syringe filter and analyzed by HPLC. The developed calibration curve was used to determine the amount of drug in the solution (Asol). The mobile phase was the same as that used for the calibration curve (24, 25, 28-30).

Equation (1) below was used to determine the percent amount of drug loaded.

$$(\%) \, DL = ((A\text{sol})/(A\text{Np})) \times 100\% \quad \text{Eq. 1}$$

Encapsulation Efficiency (FE)

Nanoparticle Encapsulation efficiency was determined under the assumption that the total amount of drug encapsulated equals the initial amount of drug incorporated in nanoparticle synthesis (Aprep), minus amount of drug found in the supernatant (Asup). (%) encapsulation efficiency was calculated with equation (2).

$$(\%) \, EE = (((A\text{prep}) - (A\text{sup}))/(A\text{prep})) \times 100\% \quad \text{Eq. 2}$$

Nanoparticle % Yield

The percent yield of synthesized nanoparticles was calculated based on the weight of freeze-dried nanoparticles (WNP) and the total weight of all materials used in the formulation (WForm) using the equation (3)

$$\% \, \text{Yield} = ((WNP)/(W\text{Form})) \times 100\% \quad \text{Eq. 3}$$

Development of Calibration Curve for In Vitro Availability Studies

Both 17-AAG and paclitaxel were dissolved in ethanol at concentrations of 0.5 µg/mL, 2.5 µg/mL, 5 µg/mL, 10 µg/mL, 20 µg/mL, 50 µg/mL and 100 µg/mL, and analyzed by reversed phase high performance liquid chromatography (RP-HPLC) (Agilent-Hewlett Packard 1100 series). Methanol, acetonitrile, and water (all HPLC grade) were filtered 0.2-micron nylon filter paper and used at a 30:42:28 ratio respectively as the mobile phase. 20 µl of each drug concentration was injected and analyzed at a flow rate of 1 mL/min through a C18 (4.6×150 mm, 5 µm particle size) column at 35° C. The observation wavelength of paclitaxel 227 nm; while that of 17AAG was 334 nm (31, 32). Two final calibration curves were developed (one for each drug).

In Vitro Drug Release Studies of Drug Loaded Nanoparticles

Drug availability of paclitaxel and 17AAG in vitro was studied using a dialysis method. 10 mg of freeze-dried nanoparticles was suspended in 2 mL acetic acid buffer (pH 5.0) and placed in a dialysis bag (12-14 kDa MWCO (Spectra/Por® CE)). The dialysis bag was then placed in a 15 mL Eppendorf tube, and release medium consisting of PBS buffer and 0.1% w/v polysorbate 80 (Tween 80) was added to the tube (33). The tube was placed in a lab quake shaker preset at 37° C. and rotated at 360°. Studies were done in triplicates with samples taken at time intervals, and to maintain sink conditions, an equivalent volume of fresh release medium was replaced with each sample taken out (24, 25, 28). All samples taken were each filtered with a 0.2-micron syringe filter into pre-labeled HPLC vials. Samples were then analyzed by RP-HPLC to determine the concentration of each drug present at each time period. In vitro release profiles were then developed based on the calibration curve and resulting drug concentrations for each formulation.

Optimization of Nanoparticle Formulation by Statistical Experimental Design

One challenge that faces pharmaceutical drug product development scientist is the selection of a set of conditions (formulation and process variables) which will result in a drug product with a desirable combination of properties. Essentially, this situation involves simultaneous optimization of several response variables (the desirable combination of properties) which depend upon a number of independent variables (formulation and process variables) (103). In a conventional experimental technique, the procedure is to hold all but one variable constant while changing one variable at a time. However, we know that the properties of pharmaceutical products are influenced by several variables. Thus, changing one factor at a time approach is not only time-consuming but also limited concerning information on interaction effects of variables on drug product properties (30).

An efficient way of planning and optimizing such experiments involves the principles of Design-of-Experiments (DOE). DOE is a statistical technique that increases the productivity of the experiments by minimizing the number of experiments involving multiple variables and maximizing the accuracy of results (an advantage of DOE is that it allows for the maximum amount of information to be extracted using the minimum number of experiments). The important property of DOE is that while several factors are varied simultaneously, each factor may be evaluated independently. Box and his co-workers have been quoted as saying "if the factors do act additively, the DOE design does the job with much more precision than one-factor-at-a-time methods and if the factors do not active additively, DOE, unlike the one-factor-at-a-time design, can detect and estimate interactions that measure this non-additivity (104, 105).

In this work the experimental objective is optimization. In optimization, it is of interest to reveal the nature of the relationship between the independent variables (formulation and process variables) and the measured responses or variables. Based on the previous studies on fabrication of nanoparticles using dispersion polymerization technique, five factors (PEG concentration, redox initiator system concentration, stirring speed of the stirrer, crosslinker concentration and the biodegradable macromonomer concentration) were considered important.

It has been decided to keep the levels of biodegradable macromonomer concentration and redox initiator system concentration constant. The remaining three factors were varied. Specification of responses was based on responses that are relevant to experimental goals: nanoparticle size, drug loading for each of the two drugs, encapsulation efficiency for each of the two drugs and release time for each of the two drugs. All the independent variables (factors) and the response variables are quantitative.

In an optimization problem, response surface method (RSM) or response surface modelling (RSM) design is often used which is different form a statistical experimental design whose objective is screening. There are several classical RSM design families. We selected the central composite face-centered design (CCF) in three independent factors and seventeen runs as shown in the table 2 below. Table 3 shows uncoded and coded levels of the independent factors. Each independent factor assumed three coded levels that were −1, 0, and +1 (Tables 2 and 3). A value was then assigned to the −1 and the +1 levels for each factor based on initial experiments to determine some constraints to allow the fabrication of good spherical particles. 0 was assigned the middle value.

All experiments were performed in random order to minimize the effects of uncontrolled factors that might introduce a bias into the measurements. Statistical analysis of the results was performed with the MODDE 12.0.1 (Umetrics, Sweden). A quadratic model was fitted to the data using multiple linear regression to be able to determine the regression coefficients and the significance of the model was tested by the analysis of variance (ANOVA) with a 95% confidence level (the ANOVA test results will show if the variance of the results is determined by the effects of the formulation factors or it represents a variance determined by experimental error). The quadratic model for each response variable will have 10 terms: one constant, three linear, three quadratic, and three two-factor interactions (Equation 4).

$$Y_n = b_0 + b_1 X_1 + b_2 X_2 + b_3 X_3 + b_{11} X_1^2 + b_{22} X_2^2 + b_{33} X_3^2 + b_{12} X_1 X_2 + b_{13} X_1 X_3 + b_{23} X_2 X_3 \quad \text{Eq. 4}$$

$Y_n$ is the dependent variable; $b_0$ is the model constant; $b_1$, $b_2$, and $b_3$ show the effects of corresponding or related variable on the response variables; $b_{11}$, $b_{22}$ and $b_{22}$ are the quadratic coefficients and $b_{12}$, $b_{13}$, and $b_{23}$ are the interaction coefficients between the studied factors.

TABLE 2

A three factor, three-level-face-centered (CCF) design with three independent variables (coded variables) showing the experimental runs.

| Experiment No | Crosslinker | PEG | Stirring speed | Point |
|---|---|---|---|---|
| 1 | −1 | −1 | −1 | Factorial |
| 2 | 1 | −1 | −1 | Factorial |
| 3 | −1 | 1 | −1 | Factorial |
| 4 | 1 | 1 | −1 | Factorial |
| 5 | −1 | −1 | 1 | Factorial |
| 6 | 1 | −1 | 1 | Factorial |
| 7 | −1 | 1 | 1 | Factorial |
| 8 | 1 | 1 | 1 | Factorial |
| 9 | −1 | 0 | 0 | Axial |
| 10 | 1 | 0 | 0 | Axial |
| 11 | 0 | −1 | 0 | Axial |
| 12 | 0 | 1 | 0 | Axial |
| 13 | 0 | 0 | −1 | Axial |
| 14 | 0 | 0 | 1 | Axial |
| 15 | 0 | 0 | 0 | Center |
| 16 | 0 | 0 | 0 | Center |
| 17 | 0 | 0 | 0 | Center |

TABLE 3

Uncoded and coded levels of the independent factors

| Factor | −1 | 0 | 1 |
|---|---|---|---|
| Crosslinker (mmol) | 0.373 | 0.466 | 0.4915 |
| Stirring Speed (rpm) | 100 | 200 | 300 |
| PEG (mmol) | 0.898 | 1.0105 | 1.123 |

Statistical Experimental Design: Central Composite Face-Centered Design (CCF)

A DOE approach was used to systematically investigate the effects of PEG concentration, stirrer speed, and crosslinker concentration (which were established to be the important input formulation variables in prior work on dispersion polymerization).

A total of 17 different nanoparticles fabrication experiments (including three replicates of the center points to provide an estimate of replicate error: the replicated experiments enable the performance of a lack of fit test) were carried out based on CCF design. The factors and data are shown in Tables 3 and 4 respectively.

Macromonomer and the initiator system were held constant, making the experimental design to be central composite face-centered design (CCF) in three independent factors and seventeen runs. The response variables are nanoparticle size, paclitaxel drug loading, 17-AAG drug loading, paclitaxel encapsulation efficiency, 17-AAG encapsulation efficiency, release time for paclitaxel and release time for 17-AAG.

TABLE 4

Factors used in the fabrication of nanoparticles.

| Experiment No | Run Order | Crosslinker (mmol) | PEG (mmol) | Stirring speed (rpm) | Macromonomer (mmol) | Initiator System (mmol) |
|---|---|---|---|---|---|---|
| 1 | 6 | 0.373 | 0.898 | 100 | 0.28 | 0.594 |
| 2 | 17 | 0.466 | 0.898 | 100 | 0.28 | 0.594 |
| 3 | 12 | 0.373 | 1.123 | 100 | 0.28 | 0.594 |
| 4 | 11 | 0.466 | 1.123 | 100 | 0.28 | 0.594 |
| 5 | 16 | 0.373 | 0.898 | 300 | 0.28 | 0.594 |
| 6 | 9 | 0.466 | 0.898 | 300 | 0.28 | 0.594 |
| 7 | 15 | 0.373 | 1.123 | 300 | 0.28 | 0.594 |
| 8 | 7 | 0.466 | 1.123 | 300 | 0.28 | 0.594 |
| 9 | 8 | 0.373 | 1.0105 | 200 | 0.28 | 0.594 |
| 10 | 13 | 0.466 | 1.0105 | 200 | 0.28 | 0.594 |
| 11 | 4 | 0.4195 | 0.898 | 200 | 0.28 | 0.594 |
| 12 | 3 | 0.4195 | 1.123 | 200 | 0.28 | 0.594 |
| 13 | 10 | 0.4195 | 1.0105 | 100 | 0.28 | 0.594 |
| 14 | 1 | 0.4195 | 1.0105 | 300 | 0.28 | 0.594 |
| 15 | 2 | 0.4195 | 1.0105 | 200 | 0.28 | 0.594 |
| 16 | 5 | 0.4195 | 1.0105 | 200 | 0.28 | 0.594 |
| 17 | 14 | 0.4195 | 1.0105 | 200 | 0.28 | 0.594 |

Nanoparticle Characterization: Response Variables

Particle Size Analysis: The particle sizes and the poly dispersity index of all the 17 formulations were determined by dynamic light scattering, which is a known method of particle size characterization (110). Particle sizes obtained range from 217.1 nm±1.2 to 298.4 nm±7.2, and the PDI values from 0.051±0.063 to 0.277±0.017.

Drug Loading Determination: The drug loading of each drug (paclitaxel and 17AAG) were determined by expressing the amount of drug in solution analyzed by HPLC as a percentage of the freeze-dried nanoparticles analyzed (26, 27, 111). Percent drug loading was found to range between 1.53±0.38 to 1.99±0.81 for paclitaxel, and 0.83±0.53 to 1.00±0.26 for 17AAG.

Encapsulation Efficiency Determination: The encapsulation efficiency of each drug was obtained by expressing the difference between the amount of drug incorporated into the nanoparticle during synthesis and that found in the supernatant (after centrifugation) determined by HPLC analysis, as a percentage of the amount of drug incorporated into the nanoparticle during synthesis (Equation 2) (26, 27, 111). The percent encapsulation efficiency determined ranged between 89.78 to 99.95 for paclitaxel, and 90.49 to 98.98 for 17AAG.

Drug Release Time: Finally, the in vitro drug release profile of each drug for all 17 formulations was determined by HPLC analysis to obtain the maximum release time for each drug as shown in table 6. The drug release studies were done in an acetate buffer release media (pH 5.5) as explained in the methodology, in order to mimic release of the drugs in the tumor microenvironment. Nanoparticles were fabricated with the synthesized pH sensitive crosslinker which has an acetal linkage that hydrolyzes in acidic environments. The hydrolysis of the crosslinker which interconnects the macromonomer forming the nanoparticle, causes the degradation of the nanoparticle, releasing the drug (109, 112, 113).

TABLE 5

Data on nanoparticle properties (Response variables to the factors shown in Table 5, where P = paclitaxel, and G = 17AAG; ε = standard deviation)

| Exp. No | Run Order | Particle size (nm) | Drag Loading P (%) | Drag Loading G (%) | Encapsulation Efficiency (Paclitaxel) (%) | Encapsulation Efficiency (17-AAG) (%) | Release Time Drag (Paclitaxel) (hrs) | Release TimeDrug (17-AAG) (hrs) |
|---|---|---|---|---|---|---|---|---|
| 1 | 6 | 291.7 | 1.53 | 0.83 | 98.76 | 97.99 | 50.7 | 24.3 |
| 2 | 17 | 298.4 | 1.62 | 0.89 | 98.47 | 97.61 | 48 | 48 |
| 3 | 12 | 267.5 | 1.64 | 0.88 | 90 | 90.49 | 60.8 | 24 |
| 4 | 11 | 270.6 | 1.76 | 0.95 | 99.75 | 98.8 | 74 | 59 |
| 5 | 16 | 228.6 | 1.58 | 0.88 | 99.95 | 99.37 | 49 | 49 |
| 6 | 9 | 261.2 | 1.53 | 0.85 | 95.85 | 93.77 | 49 | 25 |
| 7 | 15 | 217.1 | 1.99 | 0.98 | 99.87 | 98.93 | 48 | 48 |
| 8 | 7 | 260.8 | 1.79 | 0.93 | 99.93 | 98.98 | 72 | 72 |
| 9 | 8 | 229 | 1.57 | 0.95 | 92.45 | 91.75 | 48 | 24 |
| 10 | 13 | 289.6 | 1.71 | 0.85 | 97.3 | 95.25 | 48 | 32 |
| 11 | 4 | 286.1 | 1.72 | 0.9 | 89.78 | 91.5 | 72 | 36 |
| 12 | 3 | 255.3 | 1.94 | 0.86 | 97.91 | 95.68 | 68 | 48 |
| 13 | 10 | 250.3 | 1.85 | 0.97 | 99.22 | 97.63 | 71 | 24 |
| 14 | 1 | 288.7 | 1.65 | 0.92 | 97.02 | 97.58 | 74 | 48.3 |
| 15 | 2 | 249.4 | 1.78 | 1 | 94.47 | 96.88 | 70 | 28 |
| 16 | 5 | 235.6 | 1.87 | 0.96 | 96.98 | 97.75 | 73 | 24 |
| 17 | 14 | 232.4 | 1.87 | 1 | 98.69 | 97.04 | 69 | 22 |
| ε | | ±0.2-±10.6 | ±0.38-±0.81 | ±0.53-±0.76 | | | | |

Nanoparticle Zeta Potential and Surface Morphology

Zeta Potential is a measure of the effective electric charge on the surface of the nanoparticle which determines the stability of the nanoparticle in suspension (114). It is a basic phenomenon in chemistry that like charges repel. Thus, negatively charged nanoparticles will repel each other, making them less likely to aggregate in suspension (115). The tendency of cells to internalize nanoparticles greatly depends on the overall surface charge of surrounding fluids which arise from the cell-nanoparticle surface charge interactions (116). Studies have been done to prove that nanoparticle surface charge influences cellular uptake (117). Higher cellular uptake and lower protein adsorption was detected with negatively charged than with positively charged nanoparticles by Patil et. al (118).

Zeta potential of the synthesized nanoparticles ranged from −22.60 mV±0.46 to −43.49 mV±1.89 (Table), indicating that they are likely to facilitate cellular uptake and less likely to aggregate in suspension.

Figure 4:
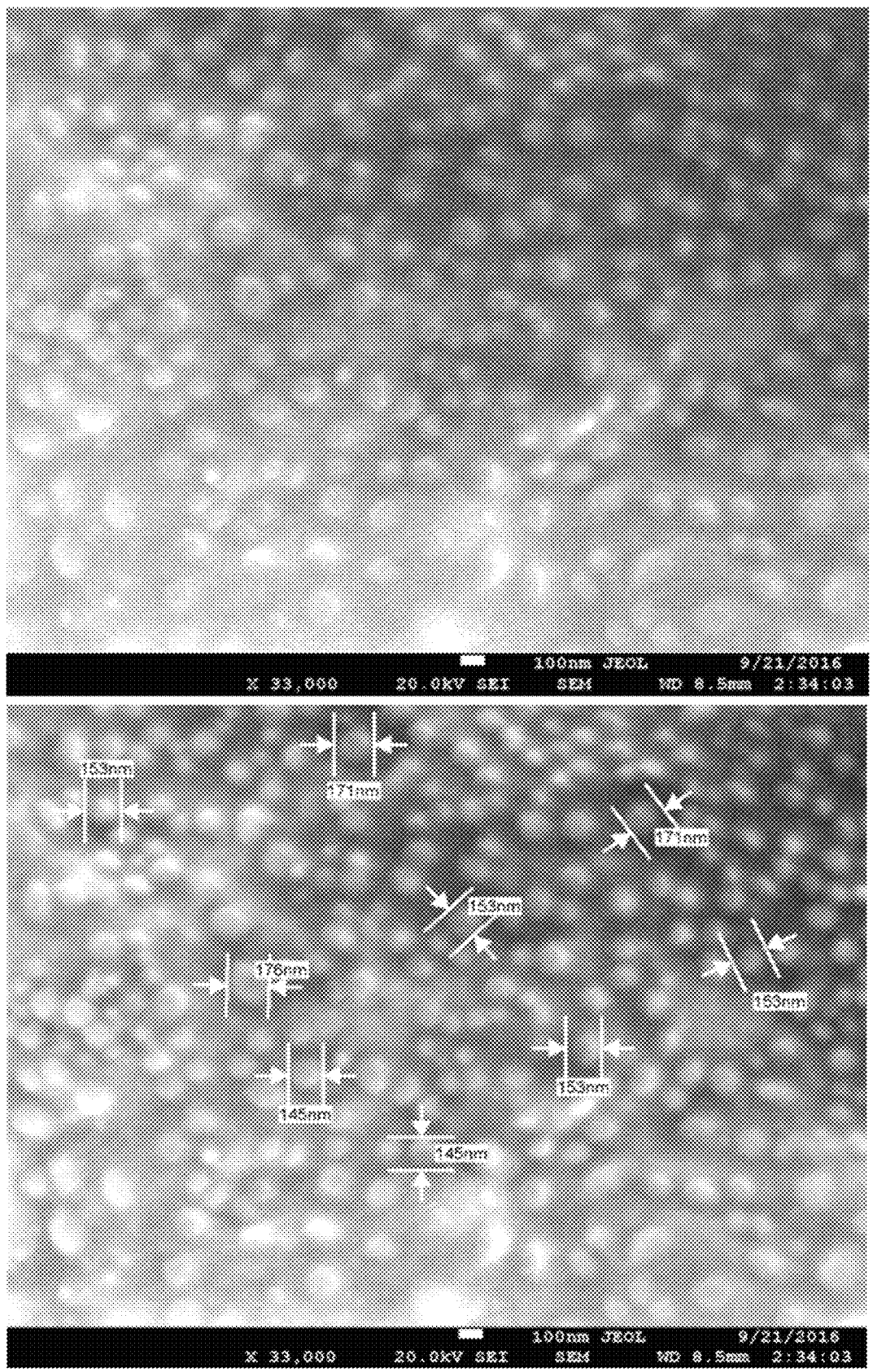
FIG. 4 shows SEM images of blank nanoparticles
Figure 5:
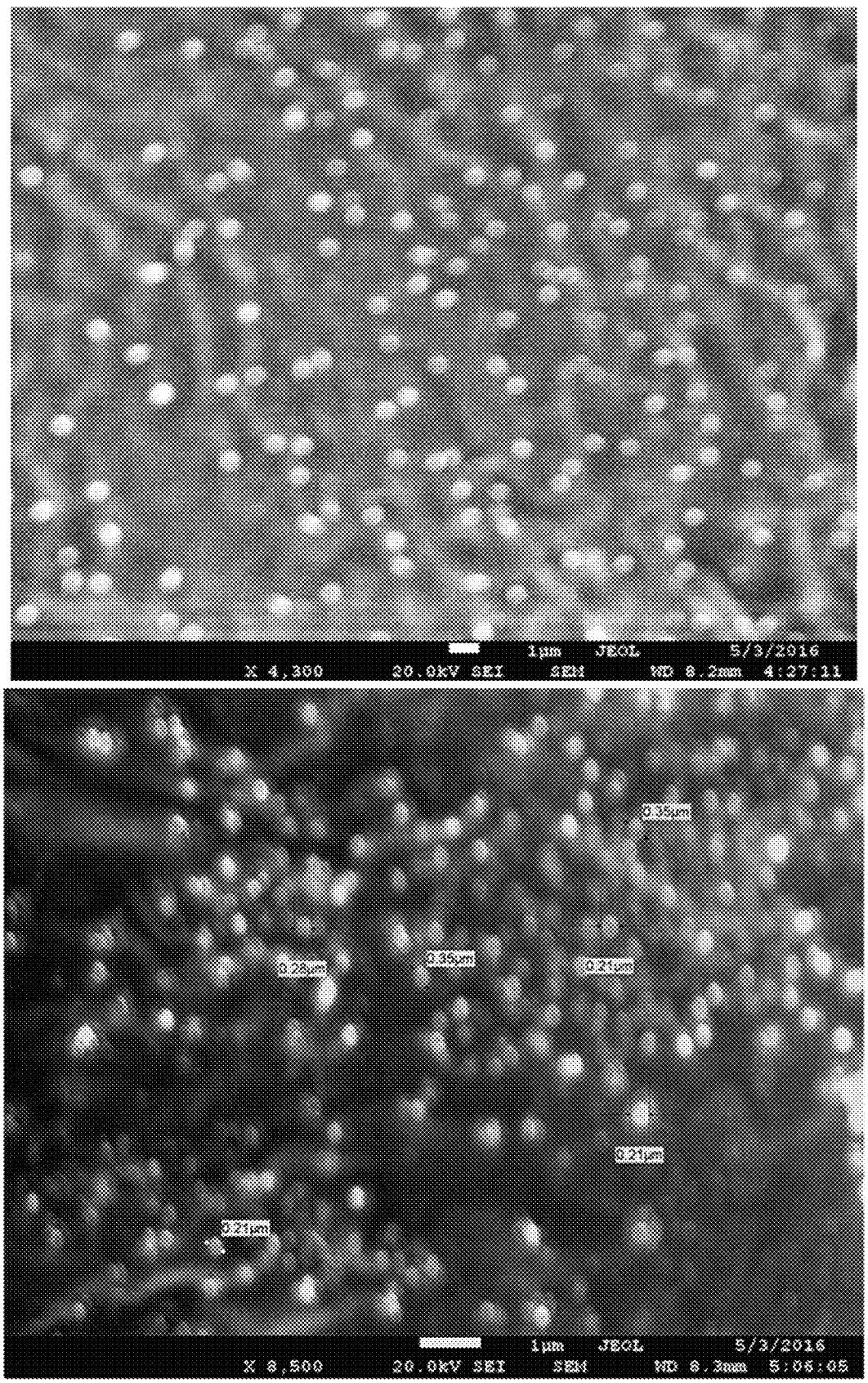
FIG. 5 shows SEM images of drug loaded nanoparticles.
Figure 6:
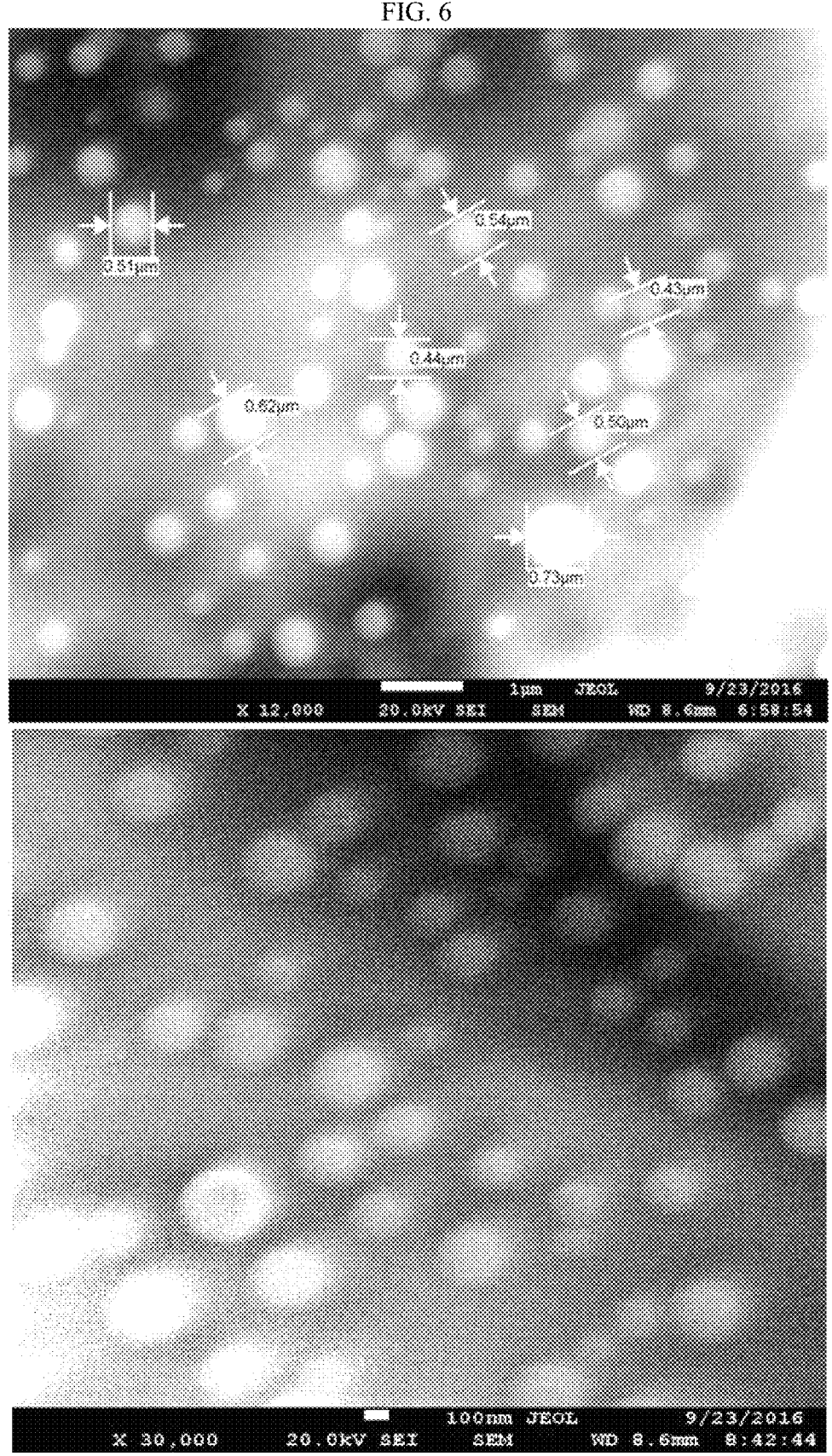
FIG. 6 shows SEM images of drug loaded nanoparticles.

The surface morphology of the nanoparticles determined by scanning electron microscopy (SEM), revealed smooth spherical nanoparticles as seen in FIGS. 4-6.

TABLE 6

Zeta potential all 17 nanoparticle formulations

| Formulation # | Zeta Potential (mV) |
|---|---|
| 1 | −35.25 ± 1.01 |
| 2 | −33.46 ± 1.68 |
| 3 | −37.21 ± 0.22 |
| 4 | −28.72 ± 1.23 |
| 5 | −27.20 ± 1.62 |
| 6 | −27.04 ± 1.75 |
| 7 | −32.69 ± 0.51 |
| 8 | −26.90 ± 1.55 |
| 9 | −30.37 ± 1.92 |
| 10 | −27.91 ± 6.98 |
| 11 | −26.40 ± 0.94 |
| 12 | −22.60 ± 0.46 |
| 13 | −36.17 ± 1.31 |
| 14 | −43.49 ± 1.89 |
| 15 | −35.81 ± 3.69 |
| 16 | −32.01 ± 1.03 |
| 17 | −35.08 ± 1.17 |

Purpose of Nanoparticle Optimization

Figure 7:
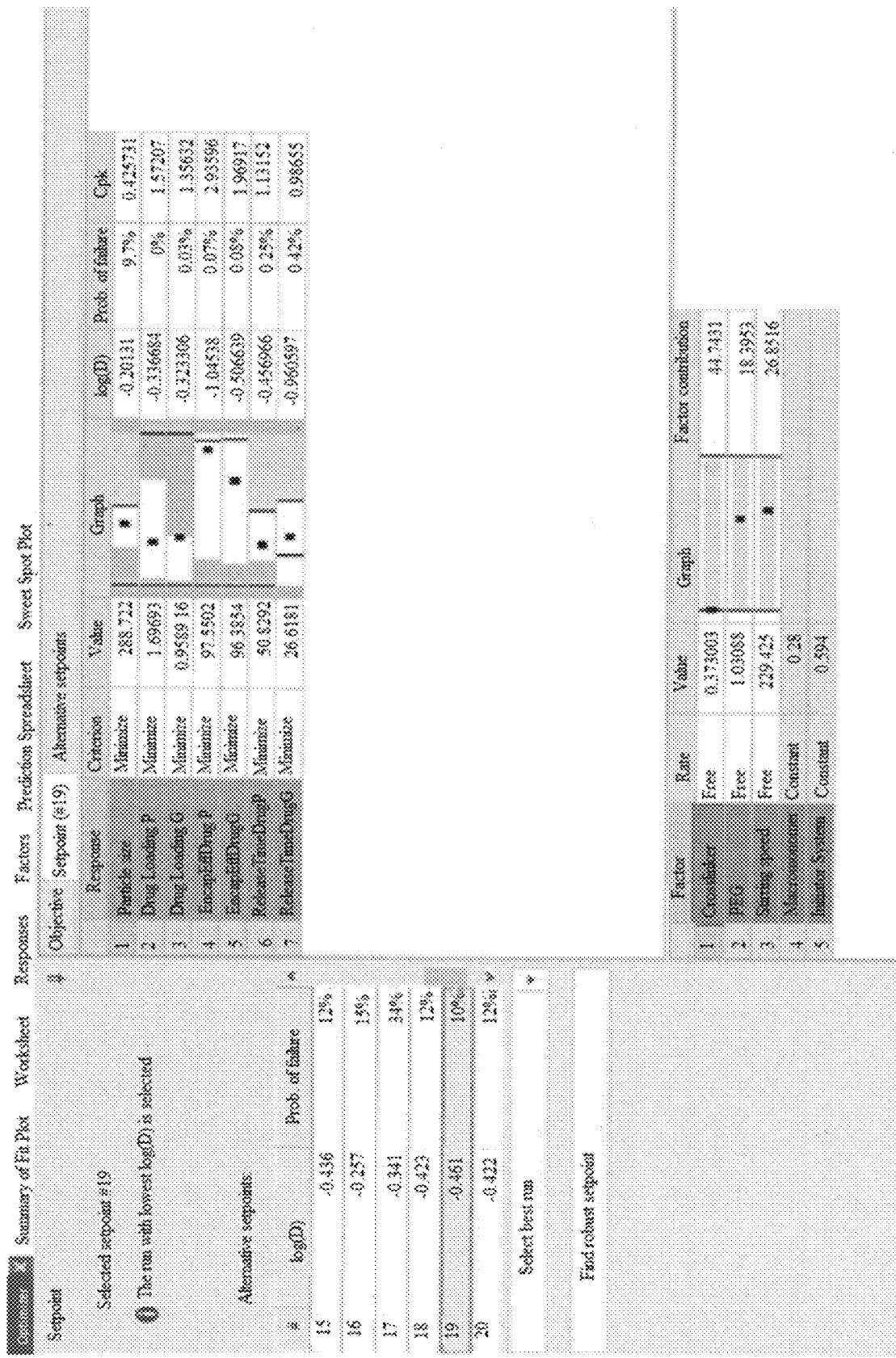
FIG. 7 shows an optimizer output following optimization.
Figure 8:
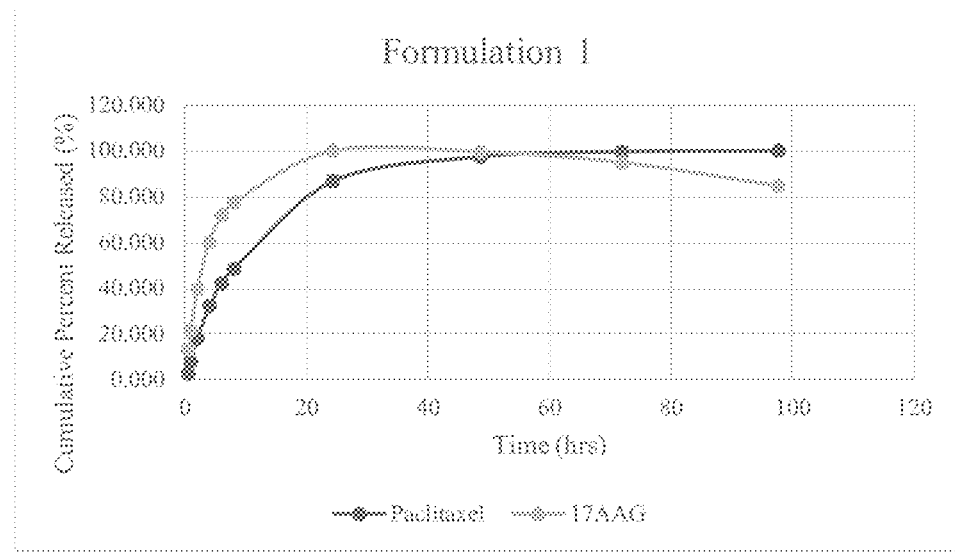
FIG. 8 shows an in vitro drug combination release profile for formulation 1.
Figure 9:
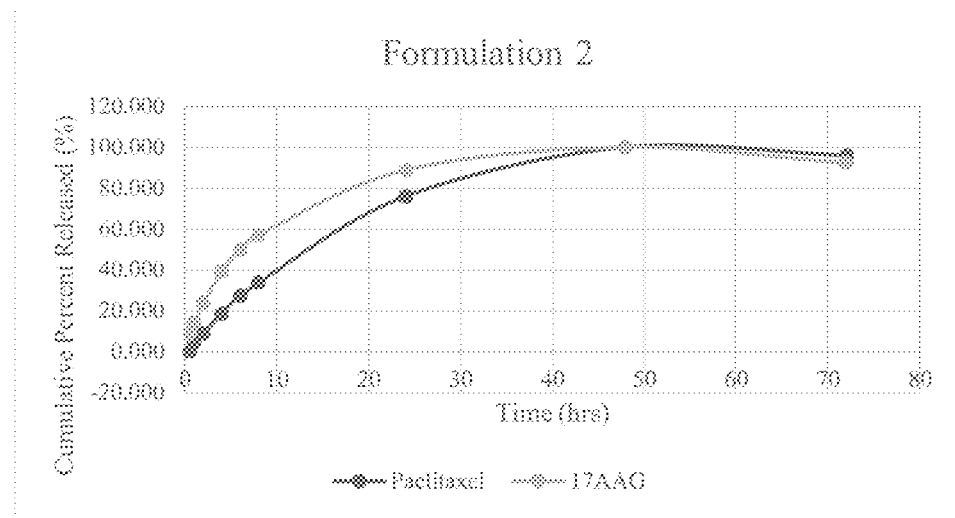
FIG. 9 shows an in vitro drug combination release profile for formulation 2.
Figure 10:
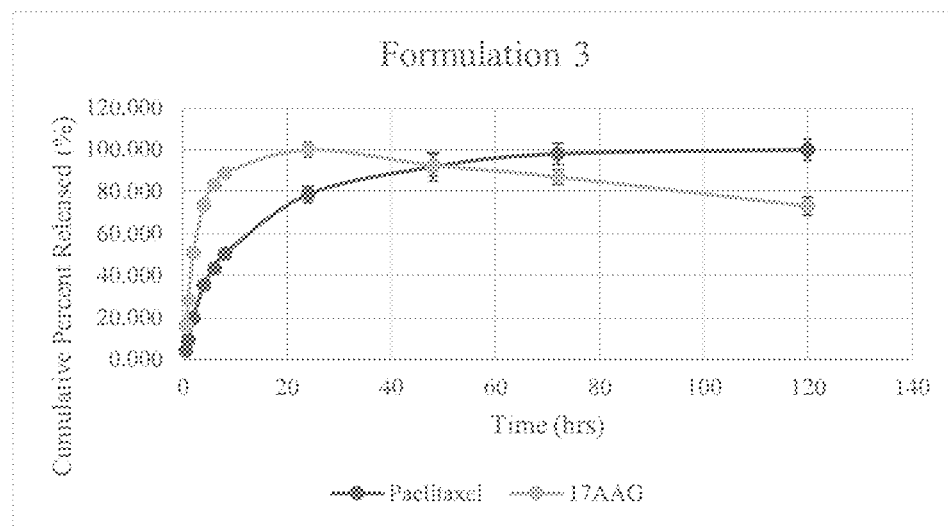
FIG. 10 shows an in vitro drug combination release profile for formulation 3.
Figure 11:
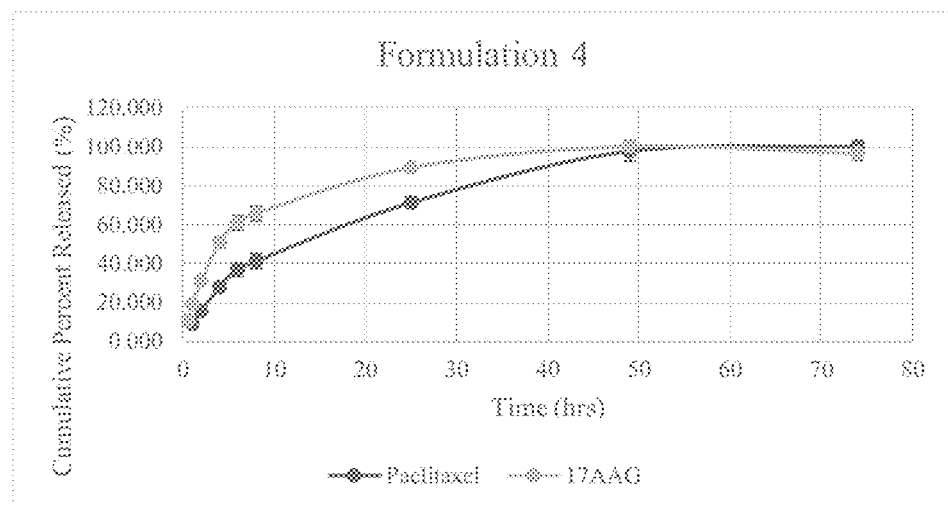
FIG. 11 shows an in vitro drug combination release profile for formulation 4.
Figure 12:
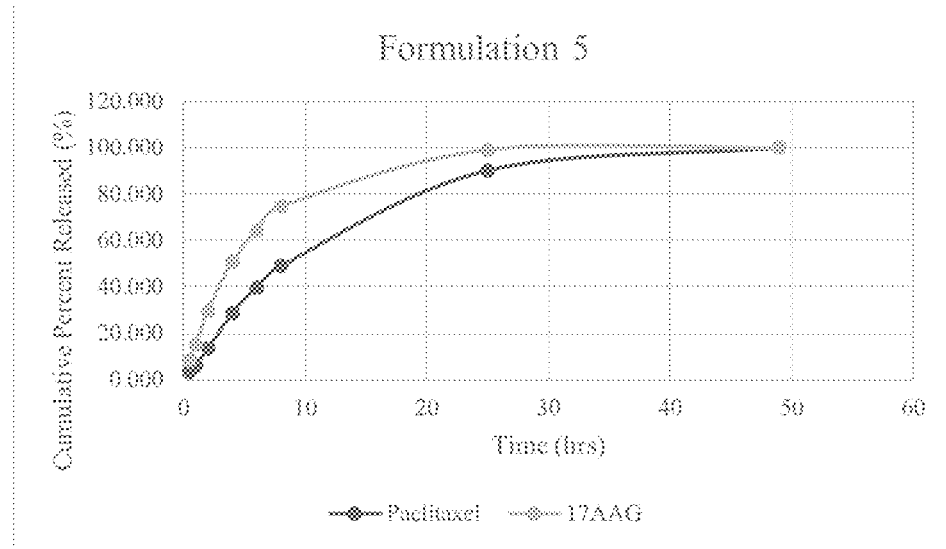
FIG. 12 shows an in vitro drug combination release profile for formulation 5.
Figure 13:
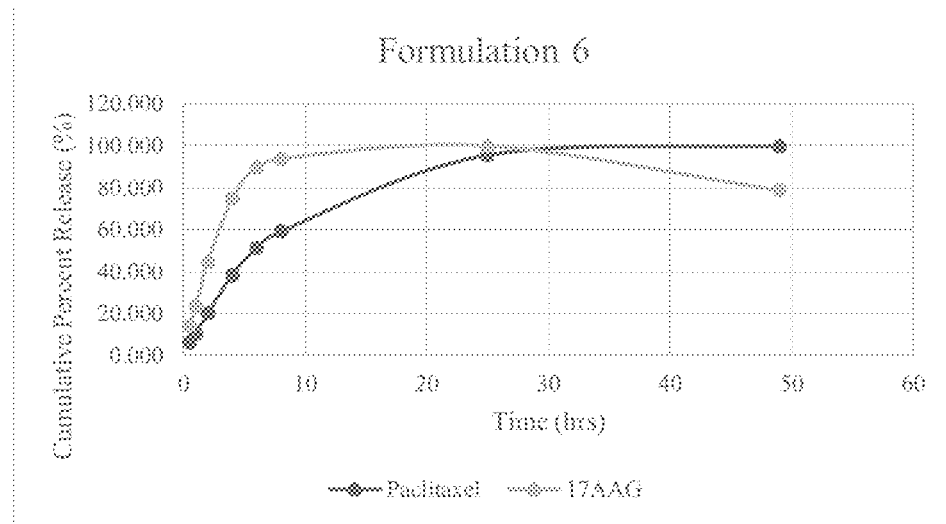
FIG. 13 shows an in vitro drug combination release profile for formulation 6.
Figure 14:
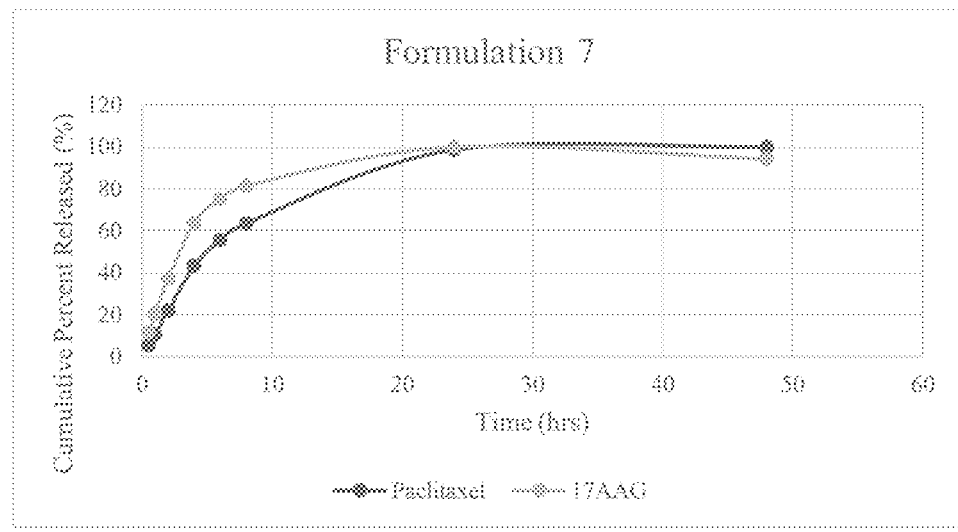
FIG. 14 shows an in vitro drug combination release profile for formulation 7.
Figure 15:
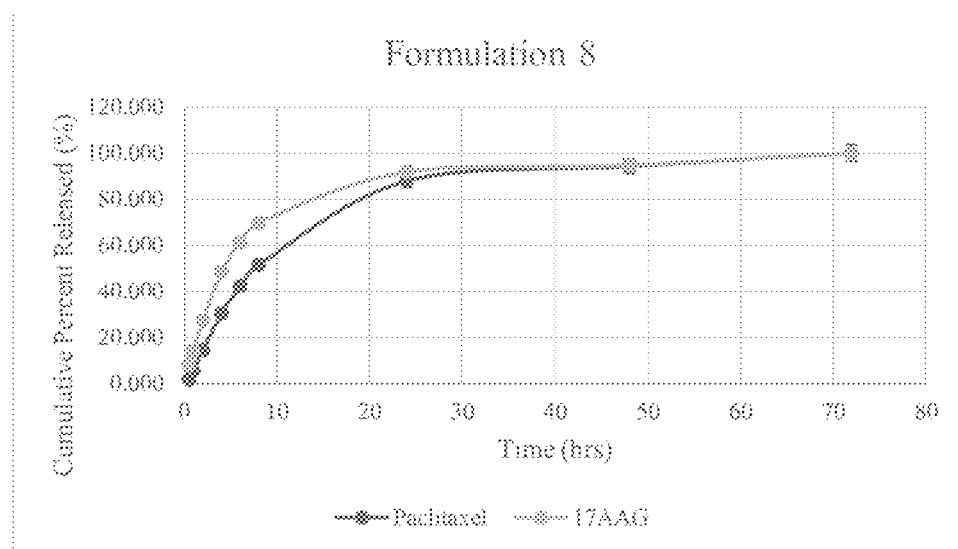
FIG. 15 shows an in vitro drug combination release profile for formulation 8.
Figure 16:
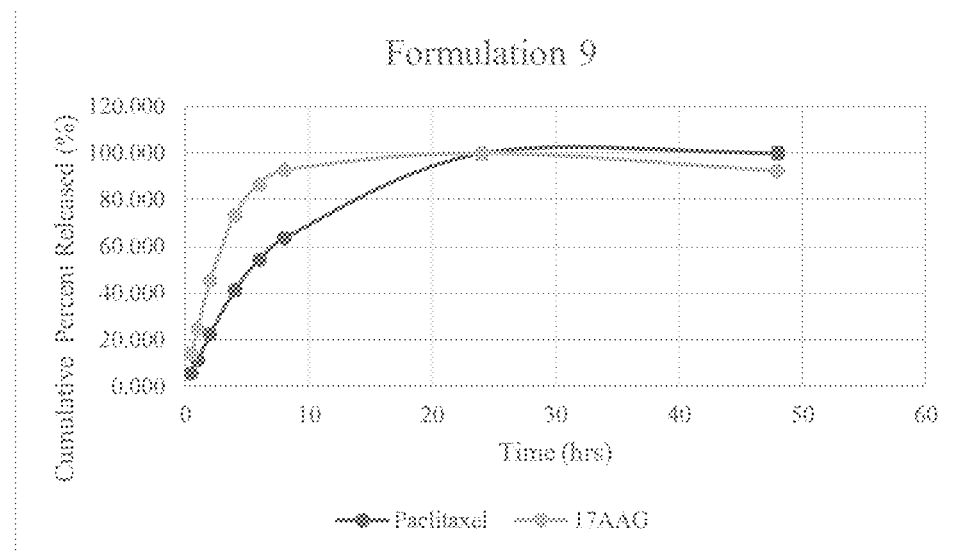
FIG. 16 shows an in vitro drug combination release profile for formulation 9.
Figure 17:
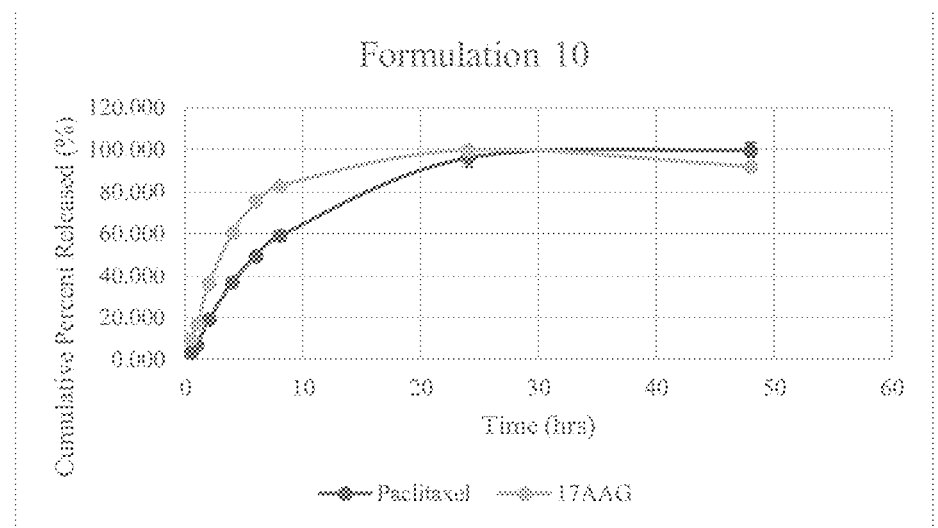
FIG. 17 shows an in vitro drug combination release profile for formulation 10.
Figure 18:
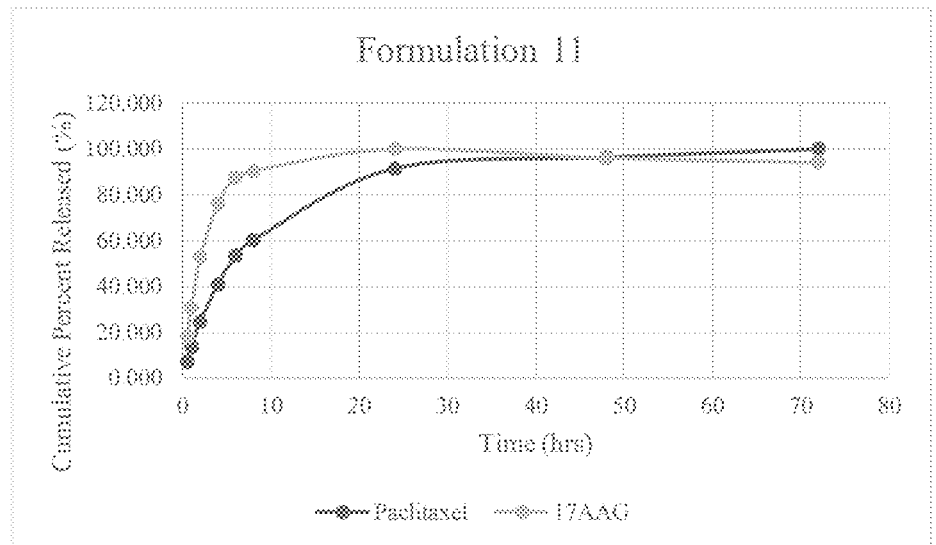
FIG. 18 shows an in vitro drug combination release profile for formulation 11.
Figure 19:
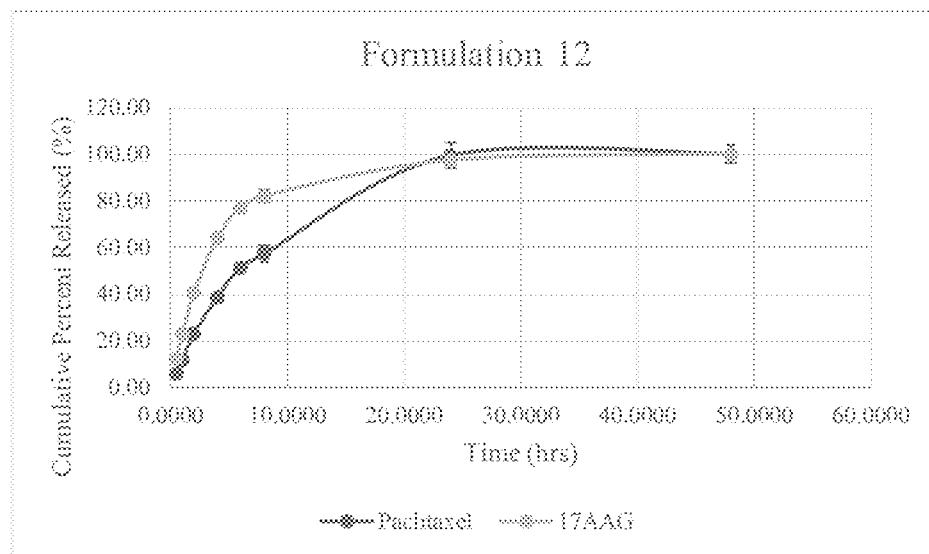
FIG. 19 shows an in vitro drug combination release profile for formulation 12.
Figure 20:
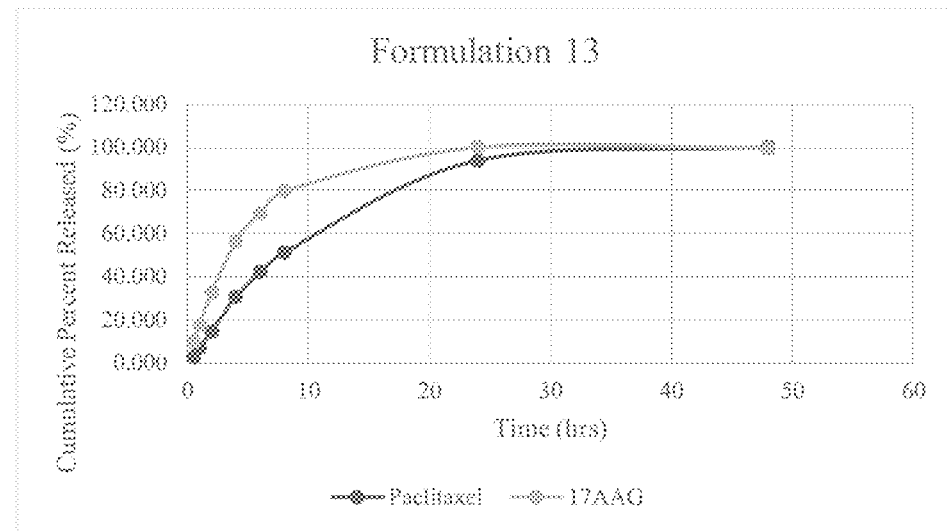
FIG. 20 shows an in vitro drug combination release profile for formulation 13.
Figure 21:
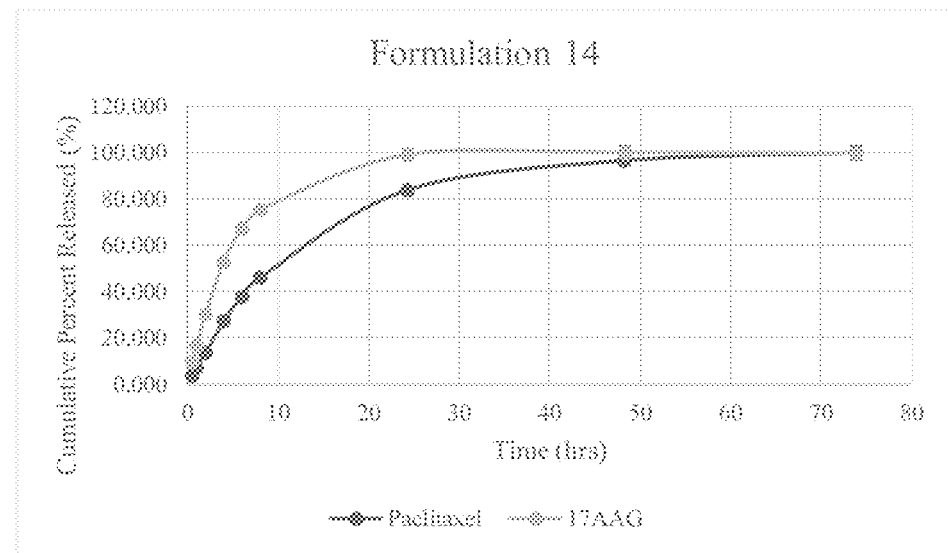
FIG. 21 shows an in vitro drug combination release profile for formulation 14.
Figure 22:
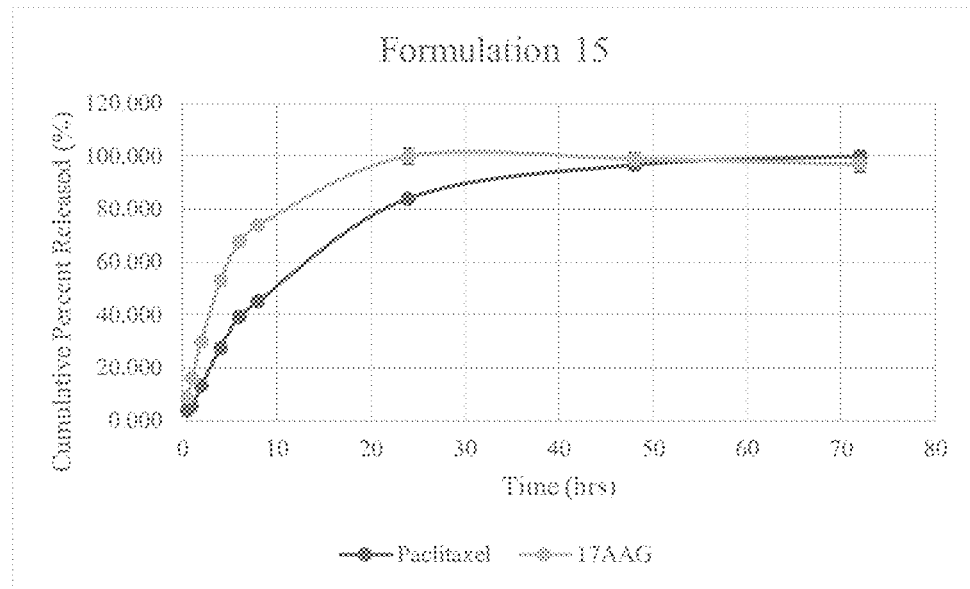
FIG. 22 shows an in vitro drug combination release profile for formulation 15.
Figure 23:
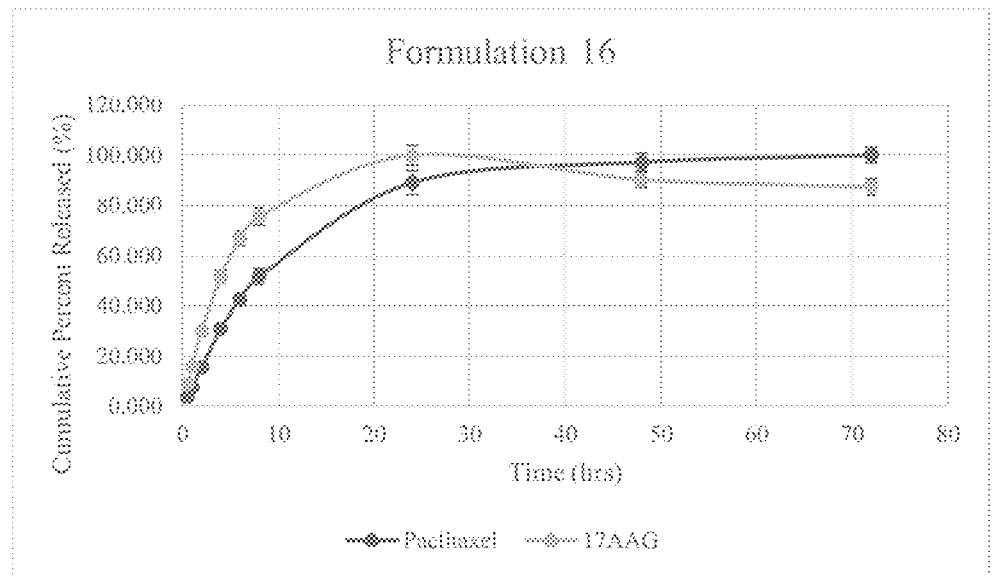
FIG. 23 shows an in vitro drug combination release profile for formulation 16.
Figure 24:
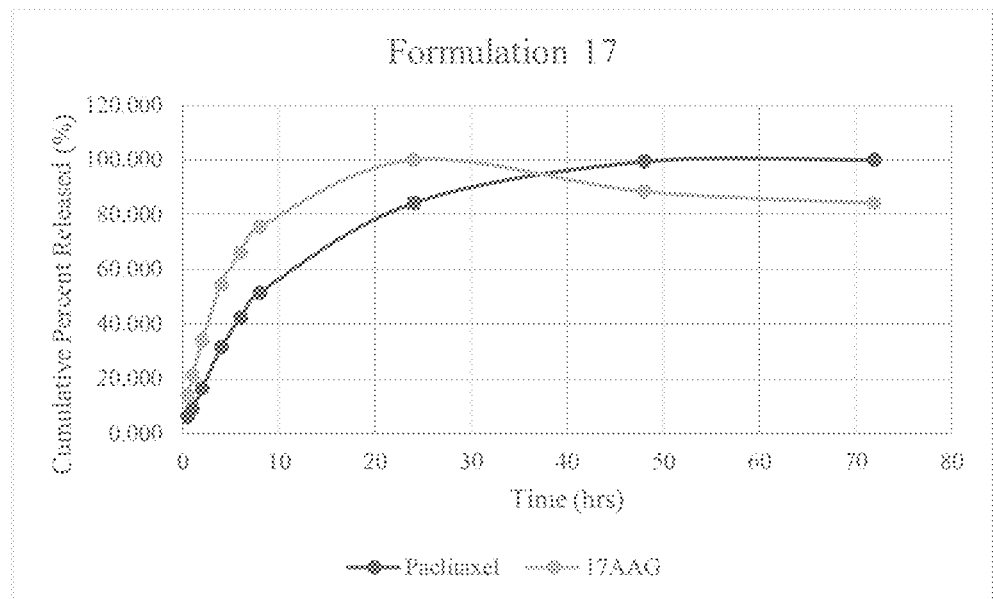
FIG. 24 shows an in vitro drug combination release profile for formulation 17.
Figure 25:
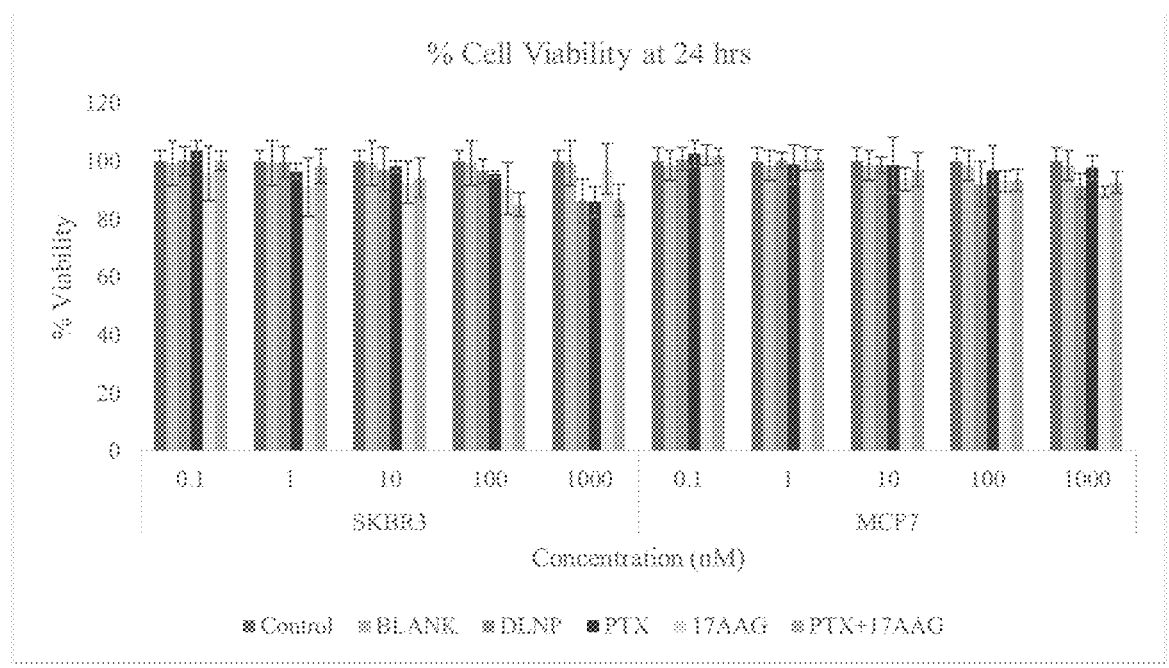
FIG. 25 shows comparison of the effect of all the treatment arms (Combination drug loaded nanoparticles (DLNP), Paclitaxel solution (PTX), 17AAG solution (17AAG) and PTX+17AAG combination drug solution) on both SKBR3 and MCF7 cell lines after 24 hours of cell exposure to treatment.
Figure 26:
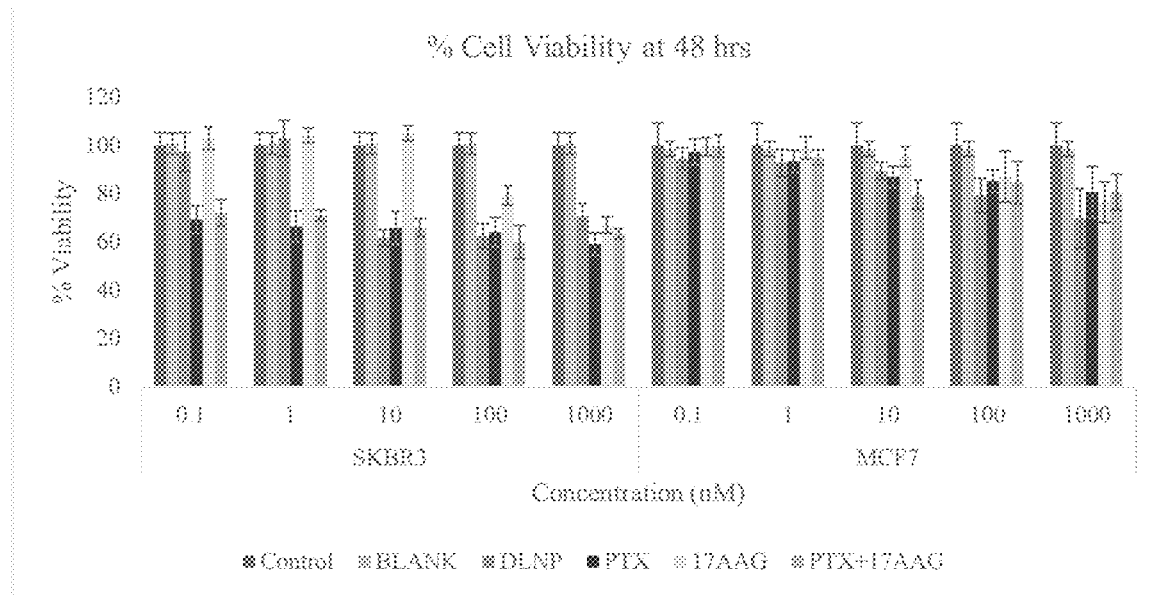
FIG. 26 shows comparison of the effect of all the treatment arms (Combination drug loaded nanoparticles (DLNP), Paclitaxel solution (PTX), 17AAG solution (17AAG) and PTX+17AAG combination drug solution) on both SKBR3 and MCF7 cell lines after 48 hours of cell exposure to treatment.
Figure 27:
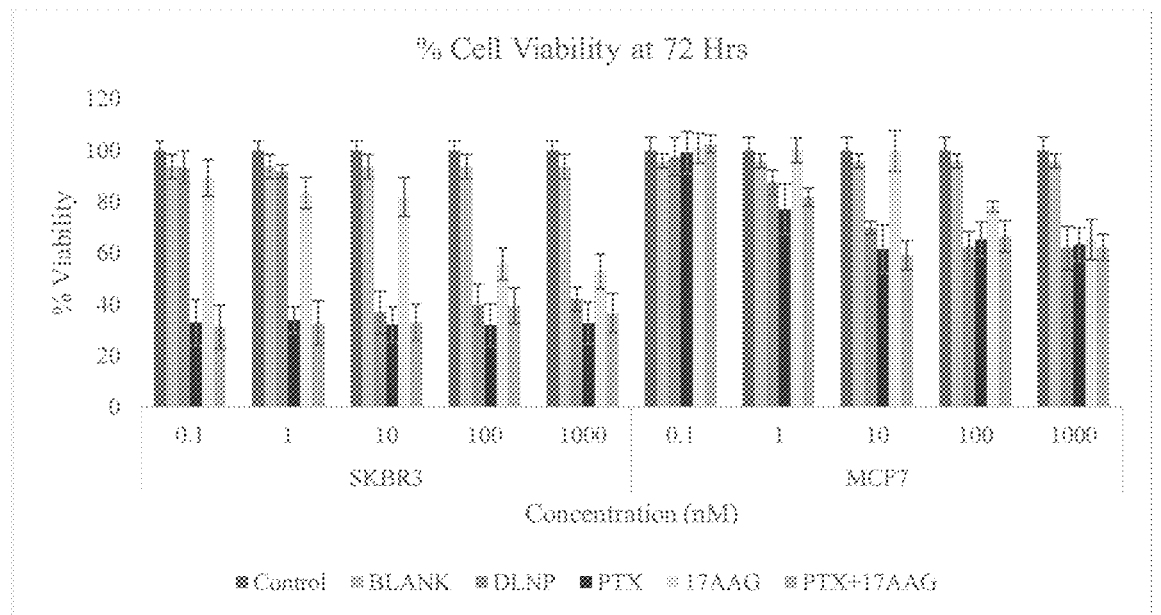
FIG. 27 shows comparison of the effect of all the treatment arms (Combination drug loaded nanoparticles (DLNP), Paclitaxel solution (PTX), 17AAG solution (17AAG) and PTX+17AAG combination drug solution) on both SKBR3 and MCF7 cell lines after 72 hours of cell exposure to treatment.
Figure 28:
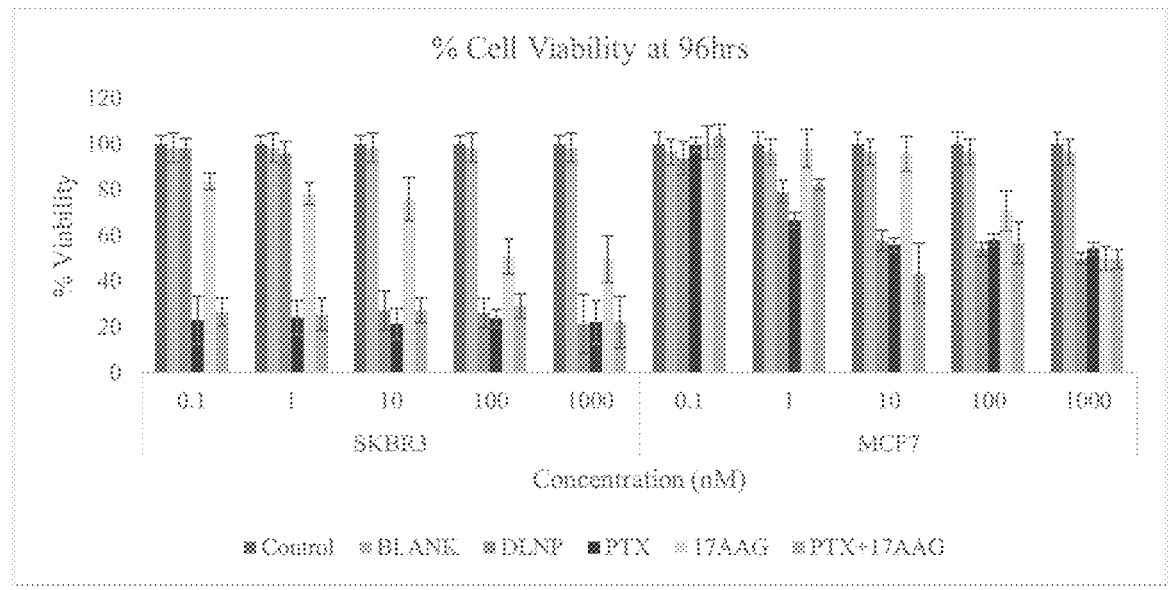
FIG. 28 shows comparison of the effect of all the treatment arms (Combination drug loaded nanoparticles (DLNP), Paclitaxel solution (PTX), 17AAG solution (17AAG) and PTX+17AAG combination drug solution) on both SKBR3 and MCF7 cell lines after 96 hours of cell exposure to treatment.

Using data obtained from all the analysis, the optimization objectives were set and an optimized formulation was generated using the optimizer option in MODDE 12.0.1 (Umetrics, Sweeden) following specifications for each of the response variables (Table 19) with predicted outcomes for particle size, drug loading, encapsulation efficiency, and release time. The run lowest log D is selected. The predicted and actual responses for the formulation generated by the optimizer are displayed in table 7. See FIG. 7 showing optimizer output following optimization.

The rationale behind the nanoparticle optimization was to design a formulation that would have low particle size, high loading and encapsulation of both drugs, with minimal release time. The idea is that particles of smaller sizes would be able to escape systemic clearance by the reticuloendothelial system (RES), allowing them to reach the target site through EPR effect. With high loading and encapsulation efficiency, there would be enough drug available in the nanoparticle for therapeutic efficacy when released. Lastly, it is possible that shorter release time of the drugs from the nanoparticles would hasten cell cytotoxicity reduce the duration of cell exposure to the drugs. Clinical trials have revealed that cancer cells develop resistance to paclitaxel over long treatment durations (121). See FIGS. 8-24.

TABLE 7

Predicted and actual responses of optimized formulation

| Response Variable | Predicted Response | Actual Response |
|---|---|---|
| Particle Size | 238.722 nm | 243.6 nm ± 0.500 |
| Drug Loading P | 1.697% | 1.71% ± 0.129 |
| Drug Loading G | 0.959% | 0.90% ± 0.056 |
| Encapsulation Efficiency P | 97.550% | 99.03% ± 0.040 |
| Encapsulation Efficiency G | 96.385% | 97.83% ± 0.009 |
| Release Time P | 50.829 hrs | 72 hrs |
| Release Time G | 26.618 hrs | 72 hrs |

Biological Studies

Since combination chemotherapy was the main focus in this study, the cytotoxic effects of two drugs in a drug delivery system and as free drugs to that of the single drugs. Paclitaxel and 17AAG were chosen for the combination mainly due to their different mechanisms of action. Also, there are several studies found in literature in which the cytotoxic effects of paclitaxel/17AAG combination have been analyzed on several cancer cell types (122, 123). Also there have been several reports of the ability of 17AAG to sensitize cells to paclitaxel (124).

In vitro cytotoxicity studies were conducted to determine the cytotoxic effect of paclitaxel (as a free drug/not in nanoparticle), 17AAG (free drug), paclitaxel+17AAG combination (as free drugs), and paclitaxel+17AAG combination loaded nanoparticles on two human breast cancer cell lines, SKBR3 and MCF7.

In preparation of the drug combination treatment, one part of each drug was halved and combined, such that each drug in the combination treatment contained half the concentration of their single drug counterparts. This means that the paclitaxel concentration in the combination treatment is 50% of the paclitaxel (single drug) treatment. In other words, the ratio of the concentration in the single drug to its respective concentration in the combination is 2:1. Also, the drug concentration ratio within the combination (paclitaxel: 17AAG) was approximately 1:1.

Toxicity is still a major problem associated with chemotherapy. Although combination chemotherapy has been proven to be more efficient than single drug therapy, in traditional combination chemotherapy high systemic toxicities and arduous side effects have been significant limitations in therapeutic efficacy. These limitations can be attributed to the use of surfactants and organic solvents (chremophor EL and ethanol) to increase the solubility of hydrophobic chemotherapeutic agents, coupled with high and frequent dosing regimen (non-nanoparticle associated) have resulted in.

For 5 days of assaying, three plates were treated for each day. The first was treated with paclitaxel solution (single drug) and paclitaxel/17AAG combination solution and second with 17AAG solution (single drug) and paclitaxel/17AAG combination solution. The last plate was treated with the combination drug loaded nanoparticle solution and paclitaxel/17AAG combination solution (free drug). Controls used were cells treated with blank nanoparticles, media only, and media containing 0.025% DMSO.

We found that the cytotoxic effect of the paclitaxel treatment and that of the combination (free drug) were similar in both SKBR3 and MCF7 cell lines (FIGS. 25-29). This suggests that the combination of paclitaxel and 17AAG yields either synergistic or potentiation effects. This is in line with in vivo studies done by Katragadda et. al in which paclitaxel/17AAG loaded micelles caused near-complete tumor growth arrest in mice bearing human ovarian cancer xenografts (125). In addition, combination index analysis done by Soni et. al (123) using the Chou and Talalay method, revealed strong synergy between paclitaxel and 17AAG at a 1:2 ratio (123).

Another important thing to note is drug combinations are found to be beneficial only at certain ratios (126). As a result, it is possible to have conflicting outcomes (synergism and antagonism) in the combination of two particular drugs as found in literature, depending on the ratios used.

Figure 29:
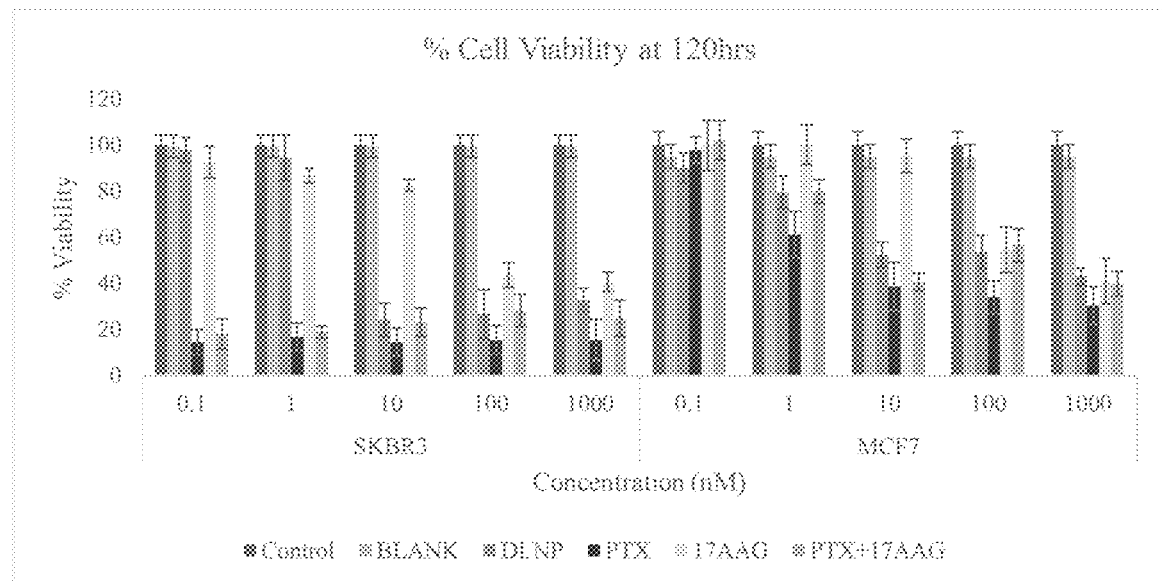
FIG. 29 shows comparison of the effect of all the treatment arms (Combination drug loaded nanoparticles (DLNP), Paclitaxel solution (PTX), 17AAG solution (17AAG) and PTX+17AAG combination drug solution) on both SKBR3 and MCF7 cell lines after 120 hours of cell exposure to treatment.

It has been also detected similar cytotoxic effects for the drug combination both in the nanoparticle and in free drug form for both cell lines. 17AAG on its own on the other hand did not show any significant cytotoxic effect at low concentrations but was able to greatly reduce cell viability at high concentrations (100 nM and 100 nM) at 120 hrs in both cell lines (FIG. 29). There was no significant decrease in viability observed in any of the control cells including the blank nanoparticles throughout the treatment durations. This indicates that the blank nanoparticles have no cytotoxic effect or contribution to the decreased viability of the treated cells.

No significant reduction in cell viability was detected in either of the cell lines at 24 hrs. However, there was less than 50% cell viability observed in SKBR3 cells within all treatment conditions at 72 hrs, and in MCF7 cells at 120 hrs. This shows that the SKBR3 cell line was more sensitive to the treatments compared to MCF7. Although both MCF7 and SKBR3 are classified as weakly aggressive cell lines, we can speculate that SKBR3 is more aggressive than MCF7 hence its higher susceptibility to the treatment (127). See FIGS. 25-29.

Effect of DLNP Treatment Duration on % Cell Viability

Figure 30:
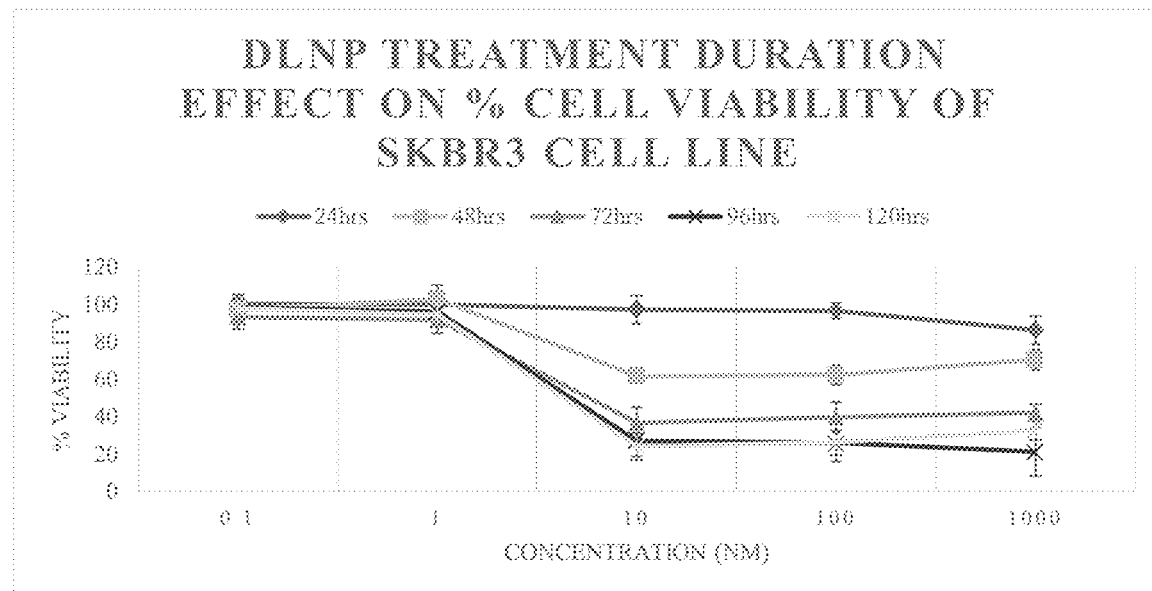
FIG. 30 shows effect of combination drug loaded nanoparticles treatment duration on the % cell viability of SKBR3 cells (n=5).
Figure 31:
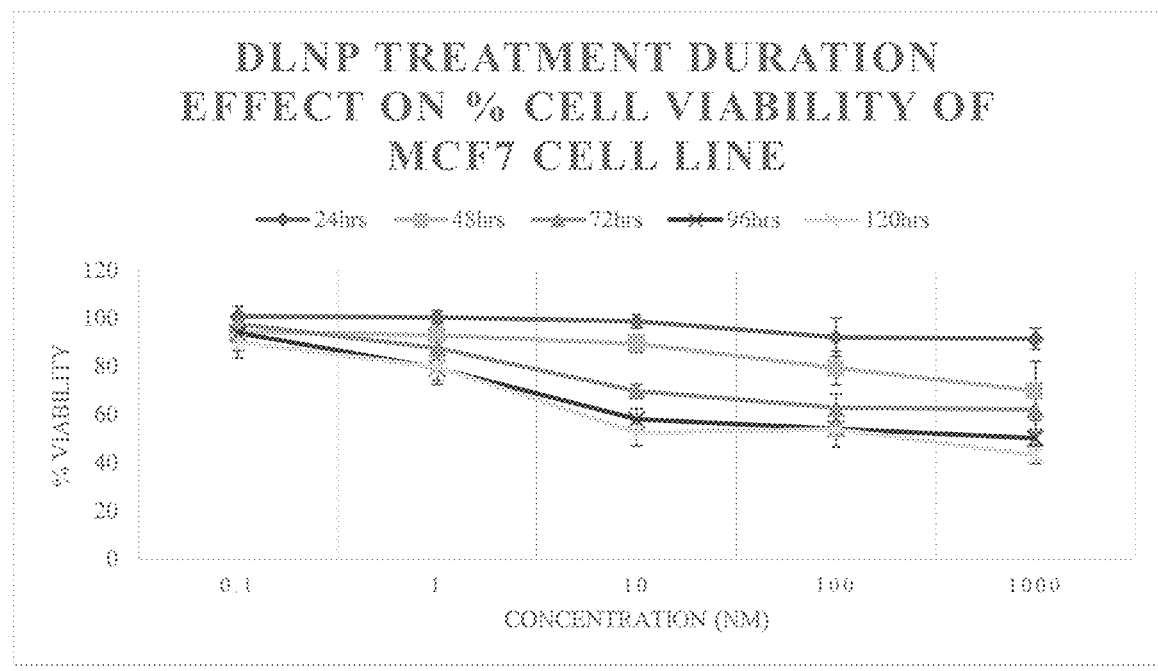
FIG. 31 shows effect of combination drug loaded nanoparticles treatment duration on the % cell viability of MCF7 cells (n=5).

The effect of combination drug-loaded nanoparticles (DLNP) with time was analyzed for both cell lines. It was observed that at 0.1 nM and 1 nM, there was no significant decrease in % cell viability within all the treatment times for both cell lines (FIGS. 30-31). This is attributed to the fact low concentrations of the drug loaded nanoparticles resulted in very low amounts of drugs being available to act on the cells.

Cytotoxic effect occurred between 1 nM and 10 nM DLNP in both cell both cell lines and across all treatment times after which the effect plateaus at higher concentrations. This plateau trend is typical of taxols as reported in literature. See FIGS. 30-31.

CONCLUSION

An acetal crosslinker hydrolysable in acidic environment was successfully synthesized and characterized by H1-NMR, FT-IR and its molecular weight confirmed by LC-MS as 408.17 g/mol. Poly epsilon caprolactone, a biocompatible and biodegradable macromonomer was also synthesized by ring opening polymerization of the caprolactone monomer and characterized by H1-NMR and FT-IR. Its number average molecular weight was determined by both H1-NMR and gel permeation chromatography (GPC) to be 1075 g/mol and 1269 g/mol respectively. The weight average molecular weight determined by GPC was 2074 g/mol.

The synthesized pH sensitive crosslinker and the macromonomer were both used in the fabrication of combination drug loaded nanoparticles by dispersion polymerization method with all the formulation components within the constraints of an upper and lower limit. In the dispersion polymerization method, a redox initiator system: benzoyl peroxide/N-phenyldiethanolamine (BPO/NPDEA) at a 1:1 ratio was used.

17 formulations within the lower and upper limit were designed and optimized using the principles of design of experiments (DoE). Optimization was done to allow us to develop a nanoparticle formulation with low particle size, high loading and encapsulation of both drugs, and minimal release time.

All synthesized nanoparticles were characterized by dynamic light scattering (DLS) to determine its particle size, and SEM, for morphology. The drug loading, encapsulation efficiency and in vitro drug release profiles at pH 5 of all the formulations were also determined.

Evaluation of all the coefficients (crosslinker, PEG, and stirring speed), in the models developed for the response variables (particle size, paclitaxel and 17AAG loading, paclitaxel and 17AAG encapsulation efficiency, and paclitaxel and 17AAG release time) revealed the significant coefficients for each response variable. For instance, crosslinker was found to significantly impact particle size, while PEG impacts drug loading (increases with increasing amounts of PEG).

In vitro cytotoxicity studies were also conducted on two breast cancer cell lines, SKBR3 and MCF7.

Cytotoxicity studies revealed that the cytotoxic effects of the paclitaxel treatment and that of the combination (free drug) were similar in both SKBR3 and MCF7 cell lines suggesting synergistic or potentiation effects. Also, since paclitaxel in the combination is half its original concentration, and still yielded the same cytotoxic effect, we have been able to reduce the dose of paclitaxel without lowering its therapeutic efficacy. 17AAG on its own was not as effective as compared to paclitaxel alone or in combination with paclitaxel.

With this benefit, it is able to maintain therapeutic efficacy with a much less intensity of the side effects brought on by each drug in the combination. This discovery promises to be a great contribution as a solution to the high toxicity and severe side effects associated with chemotherapy in general. In addition, nanotechnology as a platform for the delivery of such drug combinations eliminates the need for surfactants and organic solvents such as chremophor EL and ethanol to solubilize hydrophobic drugs prior to administration. It also facilitates dose reduction (drug loading allows us to estimate the amount of drug present at the target site), simultaneous administration of two or more drugs at the biophase, and importantly, allows us to control the drug combination ratio to avoid antagonistic effects.

While this inventive concept has been described in connection with what is presently considered to be practical example embodiments, it is to be understood that the inventive concept is not limited to the disclosed embodiments, and covers various modifications and equivalent arrangements included within the spirit and scope of the appended claims.

REFERENCES

1. Ataollahi M R, Sharifi J, Paknahad M R, Paknahad A. Breast cancer and associated factors: a review. J Med Life. 2015; 8(Spec Iss 4):6-11.
2. McGurk R, Fallowfield L, Winters Z. Information provision for patients by breast cancer teams about the side-effects of hormone treatments. European journal of cancer (Oxford, England: 1990). 2006; 42(12): 1760-7.
3. Majeed W, Aslam B, Javed I, Khaliq T, Muhammad F, Ali A, et al. Breast cancer: major risk factors and recent developments in treatment. Asian Pacific journal of cancer prevention: APJCP. 2014; 15(8):3353-8.
4. Negi P, Kingsley P A, Jain K, Sachdeva J, Srivastava H, Marcus S, et al. Survival of Triple Negative versus Triple Positive Breast Cancers: Comparison and Contrast. Asian Pacific journal of cancer prevention: APJCP. 2016; 17(8): 3911-6.
5. Iancu G, Vasile D, Iancu R C, DaviToiu D V. "Triple positive" breast cancer—a novel category Romanian journal of morphology and embryology=Revue roumaine de morphologie et embryologie. 2017; 58(1):21-6.
6. Matevossian A, Resh M. Hedgehog Acyltransferase as a target in estrogen receptor positive, HER2 amplified, and tamoxifen resistant breast cancer cells. Mol Cancer. 2015; 14(1):72.
7. Chang Y Y, Kuo W H, Hung J H, Lee C Y, Lee Y H, Chang Y C, et al. Deregulated microRNAs in triple-negative breast cancer revealed by deep sequencing. Mol Cancer. 2015; 14:36.
8. Coates A S, Winer E P, Goldhirsch A, Gelber R D, Gnant M, Piccart-Gebhart M, et al. Tailoring therapies—improving the management of early breast cancer: St Gallen International Expert Consensus on the Primary Therapy of Early Breast Cancer 2015. Annals of oncology: official journal of the European Society for Medical Oncology. 2015; 26(8): 1533-46.
9. Pandey M, Sarita G P, Devi N, Thomas B C, Hussain B M, Krishnan R. Distress, anxiety, and depression in cancer patients undergoing chemotherapy. World J Surg Oncol. 2006; 4:68.
10. Pilpel Y, Sudarsanam P, Church G M. Identifying regulatory networks by combinatorial analysis of promoter elements. Nature genetics. 2001; 29(2): 153-9.
11. Lee S H, Hayano K, Zhu A X, Sahani D V, Yoshida H. Advanced Hepatocellular Carcinoma: Perfusion Computed Tomography-Based Kinetic Parameter as a Prognostic Biomarker for Prediction of Patient Survival. Journal of computer assisted tomography. 2015; 39(5):687-96.
12. Fodale V, Pierobon M, Liotta L, Petricoin E. Mechanism of cell adaptation: when and how do cancer cells develop chemoresistance? Cancer journal (Sudbury, Mass). 2011; 17(2):89-95.
13. Chou T C. Drug combination studies and their synergy quantification using the Chou-Talalay method. Cancer research. 2010; 70(2):440-6.
14. Reddy S, Raffin M, Kaklamani V. Targeting angiogenesis in metastatic breast cancer. Oncologist. 2012; 17(8): 1014-26.
15. Kipp J E. The role of solid nanoparticle technology in the parenteral delivery of poorly water-soluble drugs. International journal of pharmaceutics. 2004; 284(1-2): 109-22.
16. Mazzo D J, Nguyen-Huu J J, Pagniez S, Denis P. Compatibility of docetaxel and paclitaxel in intravenous solutions with polyvinyl chloride infusion materials. American journal of health-system pharmacy: AJHP: official journal of the American Society of Health-System Pharmacists. 1997; 54(5):566-9.
17. Donyai P, Sewell G J. Physical and chemical stability of paclitaxel infusions in different container types. Journal of oncology pharmacy practice: official publication of the International Society of Oncology Pharmacy Practitioners. 2006; 12(4):211-22.
18. Akala E O, O O. Novel stealth nanoparticles prepared by dispersion polymerization. Pharm Ind. 2013; 75(7): 1191-6.
19. Kato Y, Ozawa S, Miyamoto C, Maehata Y, Suzuki A, Maeda T, et al. Acid extracellular micro environment and cancer. Cancer Cell International. 2013; 13(1).
20. Liechty W B, Kryscio D R, Slaughter B V, Peppas N A. Polymers for drug delivery systems. Annu Rev Chem Biomol Eng. 2010; 1:149-73.
21. Gillies E R, Goodwin A P, Frechet J M. Acetals as pH-sensitive linkages for drug delivery. Bioconjugate chemistry. 2004; 15(6): 1254-63.
22. Gillies E R, Frechet J M. pH-Responsive copolymer assemblies for controlled release of doxorubicin. Bioconjugate chemistry. 2005; 16(2):361-8.
23. Themistou E, Patrickios C S. Synthesis and Characterization of Polymer Networks and Star Polymers Containing a Novel, Hydrolyzable Acetal-Based Dimethacrylate Cross-Linker. Macromolecules. 2006; 39(1):73-80.
24. Puri R, Berhe S, Akala E. pH responsive polymeric nanoparticles fabricated by dispersion polymerization as a platform for the delivery of anticancer drugs. Nanotech. 2013; 3:420-1.
25. Ogunwuyi O, Adesina S, Akala E O. D-Optimal mixture experimental design for stealth biodegradable crosslinked docetaxel-loaded poly-epsilon-caprolactone nanoparticles manufactured by dispersion polymerization. Die Pharmazie. 2015; 70(3):165-76.
26. Boguslavsky L, Baruch S, Margel S. Synthesis and characterization of polyacrylonitrile nanoparticles by dispersion/emulsion polymerization process. J Colloid Interface Sci. 2005; 289(1):71-85.
27. Shen S, Sudol E D, El-Aasser M S. Dispersion polymerization of methyl methacrylate: Mechanism of particle formation. Journal of Polymer Science. 1994; 32(6).
28. Adesina S, Wight S, Akala E. Optimization of the fabrication of novel stealth PLA based nanoparticles by dispersion polymerization using D-optimal mixture design. Drug Dev Ind Pharm. 2014; 40(11):1547-56.
29. Akala E O. Strategies for transmembrane passage of polymer-based nanostructures. In: Broz P (ed.) Polymer based nanostructures: medical applications Royal Society of Chemistry Series 9. 2010:16-80.
30. Kelkar S S, Reineke T M. Theranostics: combining imaging and therapy. Bioconjugate chemistry. 2011; 22(10):1879-903.
31. Xia X J, Peng J, Zhang P X, Jin D J, Liu Y L. Validated HPLC Method for the Determination of Paclitaxel-related Substances in an Intravenous Emulsion Loaded with a Paclitaxel-Cholesterol Complex. Indian journal of pharmaceutical sciences. 2013; 75(6):672-9.
32. Guo W, Reigan P, Siegel D, Zirrolli J, Gustafson D, Ross D. Formation of 17-allylamino-demethoxygeldanamycin (17-AAG) hydroquinone by NAD(P)H:quinone oxidoreductase 1: role of 17-AAG hydroquinone in heat shock protein 90 inhibition. Cancer research. 2005; 65(21):10006-15.
33. Pradhan R, Poudel B K, Choi J Y, Choi I S, Shin B S, Choi H G, et al. Erratum to: Preparation and evaluation of 17-allyamino-17-demethoxygeldanamycin (17-AAG)-loaded poly(lactic acid-co-glycolic acid) nanoparticles. Archives of pharmacal research. 2015; 38(5):930-1.
34. Kato Y, Ozawa S, Miyamoto C, Maehata Y, Suzuki A, Maeda T, et al. Acidic extracellular microenvironment and cancer. Cancer Cell Int. 2013; 13(1):89.
35. Gillies R J, Raghunand N, Karczmar G S, Bhujwalla Z M. MRI of the tumor microenvironment. Journal of magnetic resonance imaging: JMRI. 2002; 16(4):430-50.

36. Hu Y B, Dammer E B, Ren R J, Wang G. The endosomal-lysosomal system: from acidification and cargo sorting to neurodegeneration. Transl Neurodegener. 2015; 4:18.
37. Kamaly N, Yameen B, Wu J, Farokhzad O C. Degradable Controlled-Release Polymers and Polymeric Nanoparticles: Mechanisms of Controlling Drug Release. Chem Rev. 2016; 116(4):2602-63.
38. Hoo C M, Starostin N, West P, Mecartney M L. A comparison of atomic force microscopy (AFM) and dynamic light scattering (DLS) methods to characterize nanoparticle size distributions. Journal of Nanoparticle Research. 2008; 10(1):89-96.
39. Kashi T S, Eskandarion S, Esfandyari-Manesh M, Marashi S M, Samadi N, Fatemi S M, et al. Improved drug loading and antibacterial activity of minocycline-loaded PLGA nanoparticles prepared by solid/oil/water ion pairing method. Int J Nanomedicine. 2012; 7:221-34.
40. Chen B, Dai W, He B, Zhang H, Wang X, Wang Y, et al. Current Multistage Drug Delivery Systems Based on the Tumor Microenvironment. Theranostics. 2017; 7(3):538-58.
41. Koren E, Apte A, Jani A, Torchilin V P. Multifunctional PEGylated 2C5-immunoliposomes containing pH-sensitive bonds and TAT peptide for enhanced tumor cell internalization and cytotoxicity. J Control Release. 2012; 160(2):264-73.
42. Clogston J D, Patri A K. Zeta potential measurement. Methods in molecular biology (Clifton, N.J.). 2011; 697: 63-70.
43. Zhang Y, Chen Y, Westerhoff P. Crittenden J. Impact of natural organic matter and divalent cations on the stability of aqueous nanoparticles. Water Res. 2009; 43(17):4249-57.
44. Zhang Y, Yang M, Portney N G, Cui D, Budak G, Ozbay E, et al. Zeta potential: a surface electrical characteristic to probe the interaction of nanoparticles with normal and cancer human breast epithelial cells. Biomedical Microdevices. 2008:10(2):321-8.
45. Lorenz M R, Holzapfel V, Musyanovych A, Nothelfer K, Walther P, Frank H, et al. Uptake of functionalized, fluorescent-labeled polymeric particles in different cell lines and stem cells. Biomaterials. 2006; 27(14):2820-8.
46. Patil S, Sandberg A, Heckert E, Self W, Seal S. Protein adsorption and cellular uptake of cerium oxide nanoparticles as a function of zeta potential. Biomaterials. 2007; 28(31):4600-7.

What is claimed is:

1. A method for preparing a drug loaded nanoparticle comprising:
dissolving a macromonomer, a stabilizer and a crosslinker in a solvent to create a mixture;
adding an initiator system to the mixture;
dissolving a drug in an organic phase containing the mixture;
recovering a candidate drug loaded nanoparticle, and
measuring a zeta potential of the candidate drug loaded nanoparticle, and selecting the candidate drug loaded nanoparticle having the zeta potential of −22.60 mV ±0.46 to −43.49 mV ±1.89 as the drug loaded nanoparticle,
wherein the crosslinker is di (2-methacryloyloxyethoxy)-[2,4-dimethoxyphenyl]methane, and the drug comprises paclitaxel and tanespimycin (17-AAG), and
wherein the initiator system comprises azo-bis-isobutyronitrile, potassium persulfate, 2,2'-azobis-2,4-dimethylvaleronitrile, ammonium persulfate, or 2,2'-azobis [N-(2-carboxyethyl)-2-2-methylpropionamidine].

2. The method according to claim 1, wherein the macromonomer is poly(epsilon-caprolactone).

3. The method according to claim 1, wherein the stabilizer is polyethylene glycol.

4. The method according to claim 1, wherein the solvent is selected from the group consisting of dichloromethane, water, ethanol, hexane, ethyl acetate, acetone, dimethyl sulfoxide and tetrahydrofuran.

5. The method according to claim 1, wherein the macromonomer is included in an amount of 0.224 mmol to 0.279 mmol.

6. The method according to claim 1, wherein the stabilizer is included in an amount of 0.898 mmol to 1.1225 mmol.

7. The method according to claim 1, wherein the initiator system is included in an amount of 0.594 mmol to 0.744 mmol.

8. The method according to claim 1, wherein the crosslinker is included in an amount of 0.373 mmol to 0.466 mmol.

9. A composition comprising the drug loaded nanoparticle prepared by the method according to claim 1.

10. The composition according to claim 9, wherein the drug included in the drug loaded nanoparticle comprises paclitaxel and tanespimycin (17-AAG).

11. A method for treating cancer comprising administering the composition according to claim 9 to a subject in need thereof.

12. The method for treating cancer according to claim 11, wherein the cancer is breast cancer.

13. The method for treating cancer according to claim 12, wherein the drug included in the drug loaded nanoparticle comprises paclitaxel and tanespimycin (17-AAG).

14. The method for treating cancer according to claim 13, wherein an amount of the paclitaxel in the drug loaded nanoparticle is lower than its original concentration.

15. The method for treating cancer according to claim 13, wherein an amount of the paclitaxel in the drug loaded nanoparticle is half of its original concentration.

16. The method for treating cancer according to claim 13, wherein an amount of the tanespimycin (17-AAG) in the drug loaded nanoparticle is lower than its original concentration.

* * * * *